(12) United States Patent
Cuthbertson et al.

(10) Patent No.: US 8,404,802 B2
(45) Date of Patent: *Mar. 26, 2013

(54) PEPTIDE-BASED COMPOUNDS

(75) Inventors: Alan Cuthbertson, Oslo (NO); Bard Indrevoll, Oslo (NO)

(73) Assignee: GE Healthcare AS, Oslo (NO)

( * ) Notice: Subject to any disclaimer, the term of this patent is extended or adjusted under 35 U.S.C. 154(b) by 961 days.

This patent is subject to a terminal disclaimer.

(21) Appl. No.: 12/053,829

(22) Filed: Mar. 24, 2008

(65) Prior Publication Data

US 2008/0187493 A1   Aug. 7, 2008

Related U.S. Application Data

(60) Division of application No. 10/269,575, filed on Oct. 11, 2002, now Pat. No. 7,351,790, which is a continuation of application No. PCT/NO01/00146, filed on Apr. 6, 2001.

(60) Provisional application No. 60/211,337, filed on Jun. 13, 2000.

(30) Foreign Application Priority Data

Apr. 12, 2000 (GB) .................................. 0009042.3
Oct. 12, 2000 (GB) .................................. 0025070.4

(51) Int. Cl.
*C07K 7/64* (2006.01)
(52) U.S. Cl. ....................... 530/317; 514/21.1
(58) Field of Classification Search .................... None
See application file for complete search history.

(56) References Cited

U.S. PATENT DOCUMENTS

| | | | |
|---|---|---|---|
| 4,647,447 A | 3/1987 | Gries et al. | |
| 5,364,613 A | 11/1994 | Sieving et al. | |
| 5,367,080 A | 11/1994 | Toner et al. | |
| 5,753,627 A * | 5/1998 | Albert et al. | 514/11.1 |
| 5,846,782 A | 12/1998 | Wickham et al. | |
| 7,351,790 B2 * | 4/2008 | Cuthbertson et al. | 530/317 |
| 7,608,243 B2 * | 10/2009 | Cuthbertson et al. | 424/1.69 |

FOREIGN PATENT DOCUMENTS

| | | |
|---|---|---|
| EP | 0578083 | 1/1994 |
| WO | WO89/00557 | 1/1989 |
| WO | WO90/14103 | 11/1990 |
| WO | WO95/14714 | 6/1995 |
| WO | WO95/25543 | 9/1995 |
| WO | WO95/26205 | 10/1995 |
| WO | WO96/11023 | 4/1996 |
| WO | WO97/06791 | 2/1997 |
| WO | WO97/10507 | 3/1997 |
| WO | WO97/25073 | 7/1997 |
| WO | WO97/28830 | 8/1997 |
| WO | WO98/10795 | 3/1998 |
| WO | WO98/47541 | 10/1998 |
| WO | WO98/54346 | 12/1998 |
| WO | WO98/54347 | 12/1998 |
| WO | WO99/39734 | 8/1999 |
| WO | WO99/40214 | 8/1999 |

OTHER PUBLICATIONS

Conforti, G., et al. (1992) Blood 80: 37-446.
Pasqualini, R., et al. (1997) Nature Biotechnology 15: 542-546.
Bauer, J. S., (1992) J. Cell Biol. 116: 477-487.
Gehlsen, K. R., (1988) J. Cell Biol. 106: 925-930.
Ruoslahti, J. Clin. Invest., 87: 1-5 (1991).
Haubner et al. in the J. Nucl. Med. (1999).
J. Am. Chem. Soc., 85: 2149 (1964).

* cited by examiner

*Primary Examiner* — Anish Gupta

(57) ABSTRACT

The invention relates to new peptide-based compounds for use as diagnostic imaging agents or as therapeutic agents wherein the agents comprise a targeting vector which binds to receptors associated with integrin receptors.

3 Claims, No Drawings

SEQUENCE LISTING

<160> NUMBER OF SEQ ID NOS: 5

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:
      illustrative peptide

<400> SEQUENCE: 1

Cys Asp Cys Arg Gly Asp Cys Phe Cys
 1               5

<210> SEQ ID NO 2
<211> LENGTH: 9

```
<212> TYPE: PRT
<213> ORGANISM: Artificial Sequence
<220> FEATURE:
<223> OTHER INFORMATION: Description of Artificial Sequence: synthetic
      peptide
<220> FEATURE:
<223> OTHER INFORMATION: Refer to the specification as filed for
      preferred embodiments of this peptide

<400> SEQUENCE: 2

Asp Cys Arg Gly Asp Cys Phe Cys Gly
  1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: synthetic
      peptide
<220> FEATURE:
<223> OTHER INFORMATION: Refer to the specification as filed for
      preferred embodiments of this peptide

<400> SEQUENCE: 3

Lys Cys Arg Gly Asp Cys Phe Cys Gly
  1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: MOD_RES
<222> LOCATION: (9)
<223> OTHER INFORMATION: Ahx
<220> FEATURE:
<223> OTHER INFORMATION: Refer to the specification as filed for
      preferred embodiments of this peptide

<400> SEQUENCE: 4

Asp Cys Arg Gly Asp Cys Phe Cys Xaa Lys
  1               5                  10

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: synthetic
      peptide
<220> FEATURE:
<221> NAME/KEY: MOD_RES
<222> LOCATION: (9)
<223> OTHER INFORMATION: Ahx
<220> FEATURE:
<223> OTHER INFORMATION: Refer to the specification as filed for
      preferred embodiments of this peptide

<400> SEQUENCE: 5

Asp Cys Arg Gly Asp Cys Phe Cys Xaa
  1               5
```

PEPTIDE-BASED COMPOUNDS

This application is a divisional application of U.S. application Ser. No. 10/269,575 filed Oct. 11, 2002 which is a continuation of international application number PCT/NO01/00146, filed Apr. 6, 2001, which claims priority to application No. 60/211,337 filed Jun. 13, 2000 filed in the United States and to 0009042.3 filed Apr. 12, 2000, in Great Britain and 0025070.4 filed Oct. 12, 2000 in Great Britain the entire disclosure of which is hereby incorporated by reference.

This invention relates to new peptide-based compounds and their use in therapeutically effective treatments as well as for diagnostic imaging techniques. More specifically the invention relates to the use of such peptide-based compounds used as targeting vectors that bind to receptors associated with angiogenesis, in particular integrin receptors, e.g. the $\alpha v\beta 3$ integrin receptor. Such contrast agents may thus be used for diagnosis of for example malignant diseases, heart diseases, inflammation-related diseases, rheumatoid arthritis and Kaposi's sarcoma. Moreover such agents may be used in therapeutic treatment of these diseases.

New blood vessels can be formed by two different mechanisms: vasculogenesis or angiogenesis. Angiogenesis is the formation of new blood vessels by branching from existing vessels. The primary stimulus for this process may be inadequate supply of nutrients and oxygen (hypoxia) to cells in a tissue. The cells may respond by secreting angiogenic factors, of which there are many; one example, which is frequently referred to, is vascular endothelial growth factor (VEGF). These factors initiate the secretion of proteolytic enzymes which break down the proteins of the basement membrane, as well as inhibitors which limit the action of these potentially harmful enzymes. The other prominent effect of angiogenic factors is to cause endothelial cells to migrate and divide. Endothelial cells which are attached to the basement membrane, which forms a continuous sheet around blood vessels on the contralumenal side, do not undergo mitosis. The combined effect of loss of attachment and signals from the receptors for angiogenic factors is to cause the endothelial cells to move, multiply, and rearrange themselves, and finally to synthesise a basement membrane around the new vessels.

Angiogenesis is prominent in the growth and remodeling of tissues, including wound healing and inflammatory processes. Tumors must initiate angiogenesis when they reach millimeter size in order to keep up their rate of growth. Angiogenesis is accompanied by characteristic changes in endothelial cells and their environment. The surface of these cells is remodeled in preparation for migration, and cryptic structures are exposed where the basement membrane is degraded, in addition to the variety of proteins which are involved in effecting and controlling proteolysis. In the case of tumors, the resulting network of blood vessels is usually disorganised, with the formation of sharp kinks and also arteriovenous shunts. Inhibition of angiogenesis is also considered to be a promising strategy for antitumor therapy. The transformations accompanying angiogenesis are also very promising for diagnosis, an obvious example being malignant disease, but the concept also shows great promise in inflammation and a variety of inflammation-related diseases, including atherosclerosis, the macrophages of early atherosclerotic lesions being potential sources of angiogenic factors. These factors are also involved in re-vascularisation of infracted parts of the myocardium, which occurs if a stenosis is released within a short time.

Further examples of undesired conditions that are associated with neovascularization or angiogenesis, the development or proliferation of new blood vessels are shown below. Reference is also made in this regard to WO 98/47541.

Diseases and indications associated with angiogenesis are e.g. different forms of cancer and metastasis, e.g. breast, skin, colorectal, pancreatic, prostate, lung or ovarian cancer.

Other diseases and indications are inflammation (e.g. chronic), atherosclerosis, rheumatoid arthritis and gingivitis.

Further diseases and indications associated with angiogenesis are arteriovenous alformations, astrocytomas, choriocarcinomas, glioblastomas, gliomas, hemangiomas (childhood, capillary), hepatomas, hyperplastic endometrium, ischemic myocardium, Kaposi sarcoma, macular degeneration, melanoma, neuroblastomas, occluding peripheral artery disease, osteoarthritis, psoriasis, retinopathy (diabetic, proliferative), scleroderma, seminomas, and ulcerative colitis.

Angiogenesis involves receptors which are unique to endothelial cells and surrounding tissues. These markers include growth factor receptors such as VEGF and the Integrin family of receptors. Immunohistochemical studies have demonstrated that a variety of integrins perhaps most importantly the $\alpha_v$ class are expressed on the apical surface of blood vessels [Conforti, G., et al. (1992) *Blood* 80: 37-446] and are available for targeting by circulating ligands [Pasqualini, R., et al. (1997) *Nature Biotechnology* 15: 542-546]. The $\alpha 5\beta 1$ is also an important integrin in promoting the assembly of fibronectin matrix and initiating cell attachment to fibronectin. It also plays a crucial role in cell migration [Bauer, J. S., (1992) *J. Cell Biol.* 116: 477-487] as well as tumour invasion and metastasis [Gehlsen, K. R., (1988) *J. Cell Biol.* 106: 925-930].

The integrin $\alpha v\beta 3$ is one of the receptors that is known to be associated with angiogenesis. Stimulated endothelial cells appear to rely on this receptor for survival during a critical period of the angiogenic process, as antagonists of the $\alpha v\beta 3$ integrin receptor/ligand interaction induce apoptosis and inhibit blood vessel growth.

Integrins are heterodimeric molecules in which the $\alpha$- and $\beta$-subunits penetrate the cell-membrane lipid bilayer. The $\alpha$-subunit has four $Ca^{2+}$ binding domains on its extracellular chain, and the $\beta$-subunit has a number of extracellular cysteine-rich domains.

Many ligands (e.g. fibronectin) involved in cell adhesion contain the tripeptide sequence arginine-glycine-aspartic acid (RGD). The RGD sequence appears to act as a primary recognition site between the ligands presenting this sequence and receptors on the surface of cells. It is generally believed that secondary interactions between the ligand and receptor enhance the specificity of the interaction. These secondary interactions might take place between moieties of the ligand and receptor that are immediately adjacent to the RGD sequence or at sites that are distant from the RGD sequence.

RGD peptides are known to bind to a range of integrin receptors and have the potential to regulate a number of cellular events of significant application in the clinical setting. (Ruoslahti, *J. Clin. Invest.*, 87: 1-5 (1991)). Perhaps the most widely studied effect of RGD peptides and mimetics thereof relate to their use as anti-thrombotic agents where they target the platelet integrin GpIIbIIIa.

Inhibition of angiogenesis in tissues by administration of either an $\alpha v\beta 3$ or $\alpha v\beta 5$ antagonist has been described in for example WO 97/06791 and WO 95/25543 using either antibodies or RGD containing peptides. EP 578083 describes a series of mono-cyclic RGD containing peptides and WO 90/14103 claims RGD-antibodies. Haubner et al. in the *J. Nucl. Med.* (1999); 40: 1061-1071 describe a new class of tracers for tumour targeting based on monocyclic RGD containing peptides. Biodistribution studies using whole-body autoradiographic imaging revealed however that the $^{125}$I-labelled peptides had very fast blood clearance rates and predominantly hepatobiliary excretion routes resulting in high background.

Cyclic RGD peptides containing multiple bridges have also been described in WO 98/54347 and WO 95/14714. Peptides derived from in viva biopanning (WO 97/10507) have been used for a variety of targeting applications. The sequence CDCRGDCFC (RGD-4C), with unidentified bridge positions, has been used to target drugs such as doxirubicin (WO 98/10795), nucleic acids and adenoviruses to cells (see WO 99/40214, WO 99/39734, WO 98/54347, WO 98/54346, U.S. Pat. No. 5,846,782). Peptides containing multiple cysteine residues do however suffer from the disadvantage that multiple disulphide isomers can occur. A peptide with 4 cysteine residues such as RGD-4C has the possibility of forming 3 different disulphide folded forms. The isomers will have varying affinity for the integrin receptor as the RGD pharmacophore is forced into 3 different conformations.

The efficient targeting and imaging of integrin receptors associated with angiogenesis in viva demands therefore a selective, high affinity RGD based vector which is chemically robust and stable. Furthermore, the route of excretion is an important factor when designing imaging agents in order to reduce problems with background. These stringent conditions are met by the bicyclic structures described in the present invention.

Viewed from one aspect the invention provides new peptide-based compounds as defined by formula I. These compounds have utility as vectors with affinity for integrin receptors, e.g. affinity for the integrin αvβ3.

The compounds of formula I comprise at least two bridges, where one bridge forms a disulphide bond and the second bridge comprises a thioether (sulphide) bond and where the bridges fold the vector moiety into a 'nested' configuration.

The compounds of the current invention thus have a maximum of one disulphide bridge per vector moiety. Compounds defined by the present invention are surprisingly stable in vivo and under the conditions employed during labelling, e.g. during labelling with technetium.

These new compounds may be used in therapeutically effective treatments as well as for imaging purposes.

Depending on the definitions of $R_1$, and $X_{1-8}$, formula I includes compounds comprising the moieties $(V)_k$ optionally together with the moieties L and/or R, where
V is the bicyclic vector, L is a linker moiety, R is a detectable moiety (reporter), e.g. detectable in an imaging procedure, used e.g. as a contrast agent as a $(V)_k$LR construct in vivo imaging of the human or vascularized non-human animal body (e.g. mammalian, avian or reptilian body) or used as a therapeutic agent.

The new peptide-based compounds provided by the present invention are defined by formula I:

$$[R_1-C(=O)-X_1-\underset{|}{X_2}-X_3-G-D-\underset{|}{X_4}-X_5-X_6\underset{k}{\vdash}X_7-X_8$$
$$\underset{S}{|}\underline{\hspace{3cm}}(CH_2)h$$

with S—S bridge between $X_2$ and $X_4$, and S—(CH$_2$)$h$ bridge from $R_1$ side to $X_6$.

wherein
G represents glycine, and
D represents aspartic acid, and
$R_1$ represents —(CH$_2$)$_n$— or —(CH$_2$)$_n$—C$_6$H$_4$—, preferably $R_1$, represents —(CH$_2$)—, and n represents a positive integer 1, 2, 3, 4, 5, 6, 7, 8, 9 or 10, and h represents a positive integer 1 or 2, and $X_1$ represents a bond or 1, 2, 3, 4 or 5 amino acid residues, preferably 1 or 2 amino-acid residues, wherein each amino acid residue independently is optionally derivatized with a functional side-chain, e.g. a carbohydrate moiety, suitable for modifying the pharmacokinetics or blood clearance rates of the said agents, said side-chain preferably comprising $C_{1-22}$-alkyl or $C_{1-22}$-perfluoroalkyl chains, polyethyleneglycol polymers and/or hydrophobic moieties with an affinity for serum albumin, and each amino acid residue is independently optionally binding a reporter (R) moiety suitable for in vivo imaging via i) a linker (L) moiety or ii) a chelating agent or iii) a linker (L) moiety attached to a chelating agent, and $X_1$ preferably represents aspartic acid, tyrosine, tyrosine-aspartic acid, lysine, glutamic acid, acetyl-lysine, asparagine, serine, threonine or glutamine or derivatives thereof and $X_2$ and $X_4$ represent independently an amino acid residue capable of forming a disulphide bond, preferably a cysteine or a homocysteine residue, and $X_3$ represents arginine, N-methylarginine or an arginine mimetic, preferably an arginine or a N-methylarginine residue, and $X_5$ represents a hydrophobic amino acid or derivatives thereof, preferably a tyrosine, a phenylalanine, a 3-iodo-tyrosine or a naphthylalanine residue, and more preferably a phenylalanine or a 3-iodo-tyrosine residue, and $X_6$ represents a thiol-containing amino acid residue, preferably a cysteine or a homocysteine residue, and k represents a positive integer 1, 2, 3, 4, 5, 6, 7, 8, 9 or 10, preferably the positive integer 1, 2, 3 or 4 and more preferably k represents the positive integer 1, and $X_7$ represents a linker (L) moiety or 1, 2, 3, 4, 5, 6, 7, 8, 9 or 10 amino acid residues, optionally as part of a linker (L) moiety, preferably $X_7$ represents one amino-acid residue, and each amino acid is independently optionally derivatized with a functional side-chain, e.g. a carbohydrate moiety, suitable for modifying the pharmacokinetics or blood clearance rates of the said agents, said side-chain preferably comprising $C_{1-22}$-alkyl or $C_{1-22}$-perfluoroalkyl chains, polyethyleneglycol polymers and/or hydrophobic moieties with an affinity for serum albumin, and wherein each amino acid residue optionally is independently binding a reporter (R) moiety suitable for in vivo imaging via i) a linker (L) moiety or ii) a chelating agent or iii) a linker (L) moiety attached to a chelating agent, or $X_7$ is absent, and preferably at least one individual linker (L) moiety is comprising one or more ethylene glycol units, and/or preferably $X_7$ is comprising a glycine residue or a preferred alternative is that $X_7$ is absent, and $X_8$ represents a reporter (R) moiety, or is —NH$_2$ or is absent, and any pharmaceutical acceptable salts thereof.

Especially preferred definitions of chelating agents are formulas a, b, c and d, see below. However, the compounds as defined in formula I may also comprise chelating agents as defined in Table I.

a
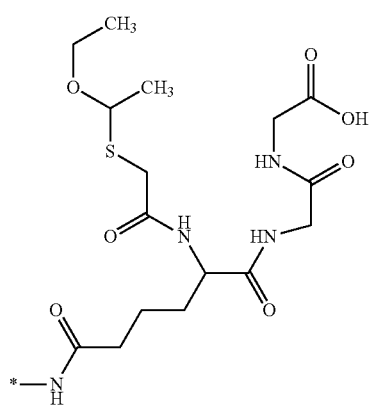
b
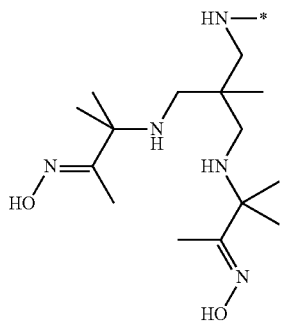
c
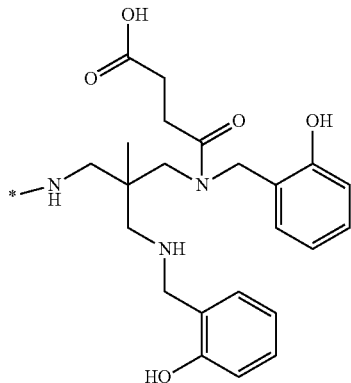
d
Preferred examples of chelating agents and linker units are shown as formulas e and f.
(e)
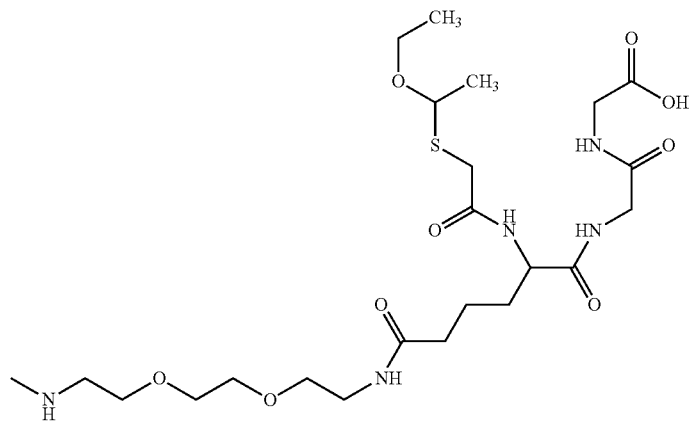
(f)
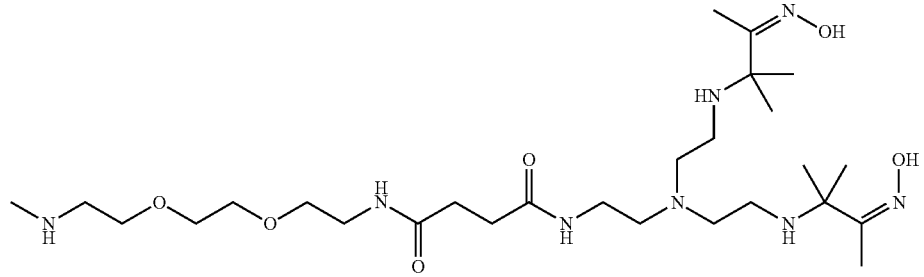

In some aspects of the invention, the chelate is a functional moiety binding to or capable of binding to a radionuclide. Preferred definitions of the chelating agents for the complexation of a nucleotide, preferably $^{99m}$technetium, are listed in the following table I.

TABLE I

| Class of ligand | Structure | Definitions |
|---|---|---|
| Amineoxime | [structure] | Y 1-8 can be H, alkyl, aryl or combinations thereof and Y4 or Y5 contains a suitable functionality such that it can be conjugated to the peptide vector - e.g. preferably alkylamine, alkylsulphide, alkoxy, alkyl carboxylate, arylamine, aryl sulphide or α- haloacetyl etc . . . X = C or N when m' = n' = 1 X = N when m' = n' = 2 |
| MAG3 type | [structure] | P = protecting group (preferably. benzoyl, acetyl, EOE); Y1, Y2 contains a suitable functionality such that it can be conjugated to the peptide vector; preferably H (MAG3), or the side chain of any amino acid, in either L or D form. |
| G4 type ligands | [structure] | Y1, Y2, Y3 - contains a suitable functionality such that it can be conjugated to the peptide vector; preferably H, or the side chain of any amino acid, in either L or D form. |
| Tetraamine ligands | [structure] | Y1-Y6 can be H, alkyl, aryl or combinations thereof where the Y1-6 groups contain one or more functional moieties such that the chelate can be conjugated to the vector - e.g. preferably alkylamine, alkylsulphide, alkoxy, alkyl carboxylate, arylamine, aryl sulphide or α-haloacetyl |

TABLE I-continued

| Class of ligand | Structure | Definitions |
|---|---|---|
| Cylam type ligands | [structure] | Y1-5 can be H, alkyl, aryl or combinations thereof and where Y1-5 groups contain one or more functional moieties such that the chelate can be conjugated to the vector - e.g. preferably alkylamine, alkylsulphide, alkoxy, alkyl carboxylate, arylamine, aryl sulphide or α-haloacetyl |
| Diaminediphenol | [structure] | Y1, Y2 - H, alkyl, aryl and where Y1 or Y2 groups contains a functional moiety such that the chelate can be conjugated to the vector - e.g. preferably alkylamine, alkylsulphide, alkoxy, alkyl carboxylate, arylamine, aryl sulphide or α-haloacetyl W = C, N m' = n' = 1 or 2 |
| HYNIC | [structure] | V = linker to vector or vector itself. |
| Amide thiols | [structure] | P = protecting group (preferably. benzoyl, acetyl, EOE); Y 1-5 = H, alkyl, aryl; or Y3 is a L or D amino acid side-chain or glycine. and the carboxylate may be used for conjugation to the vector via an amide bond. Alternatively the R$_{1-5}$ groups may contain additional functionality such that the chelate can be conjugated to the vector - e.g. alkylamine, alkylsulphide, alkoxy, alkyl carboxylate, arylamine, aryl sulphide or α-haloacetyl. |

In some aspects of the invention, the chelate is a functional moiety binding to or capable of binding a $^{18}$F isotope or an isotope of Cu, either by nucleophilic substitution, electrophilic addition reaction or by use of an chelating agent. The resulting compound may thus be used in Positron Emission Tomography (PET) Imaging.

The vector components of the vector conjugates described herein have preferably no free amino- or carboxy-termini. This introduces into these compounds a significant increase in resistance against enzymatic degradation and as a result they have an increased in vivo stability as compared to many known free peptides.

The reporter, R, may be attached to V (via L) via $X_1$ and/or $X_7$. Preferably, the point of attachment is chosen such that the biological activity of V or the binding affinity of V for its target is not substantially or not significantly reduced (in comparison with the biological activity of V or the binding affinity of V without R). Most preferably, R is attached to V.

As used herein the term 'amino acid' refers in its broadest sense to proteogenic L-amino acids, D-amino acids, chemically modified amino acids, N-methyl, Cα-methyl and amino acid side-chain mimetics and unnatural amino acids such as naphthylalanine, preferably are any naturally occurring amino acid or mimetics of such natural occurring amino acids.

Some preferred embodiments of the compounds of formula I are illustrated by Compounds II-IX below:

Compound II

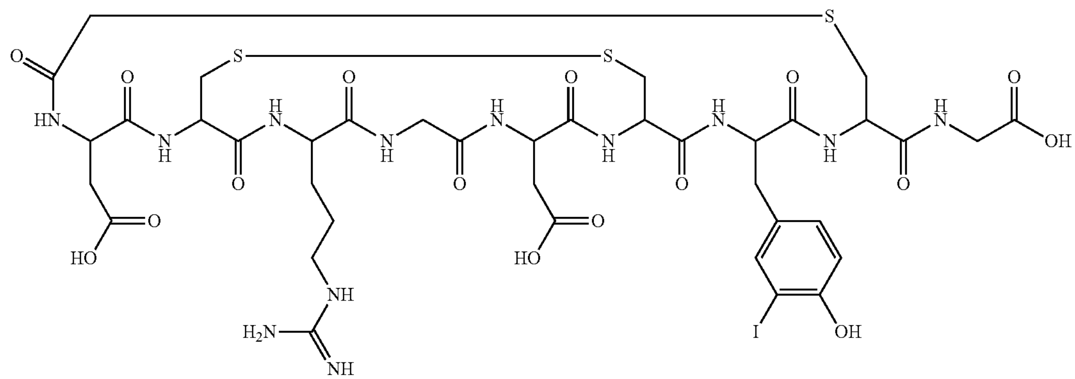

Compound III

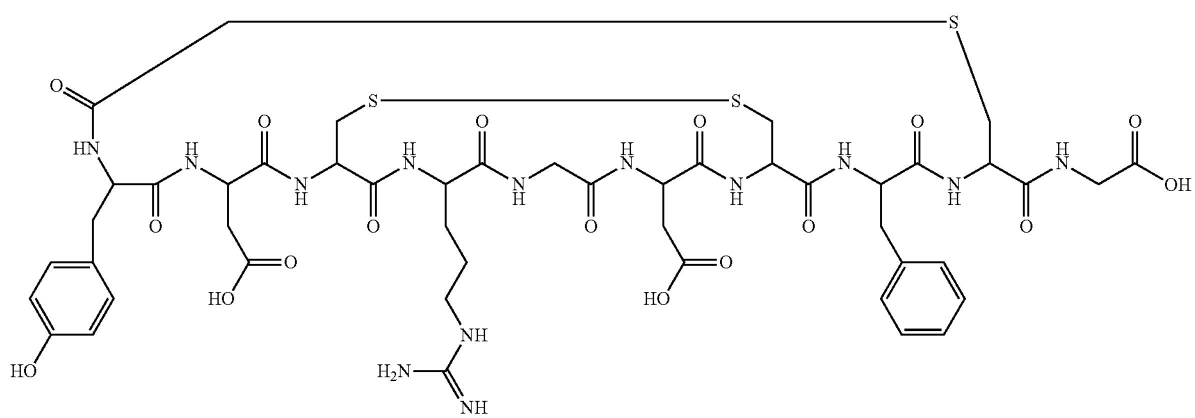

Compound IV

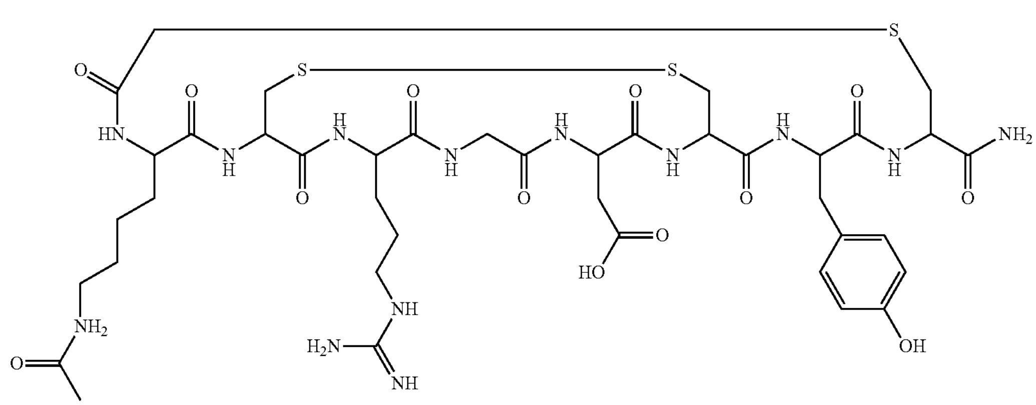

-continued
Compound V
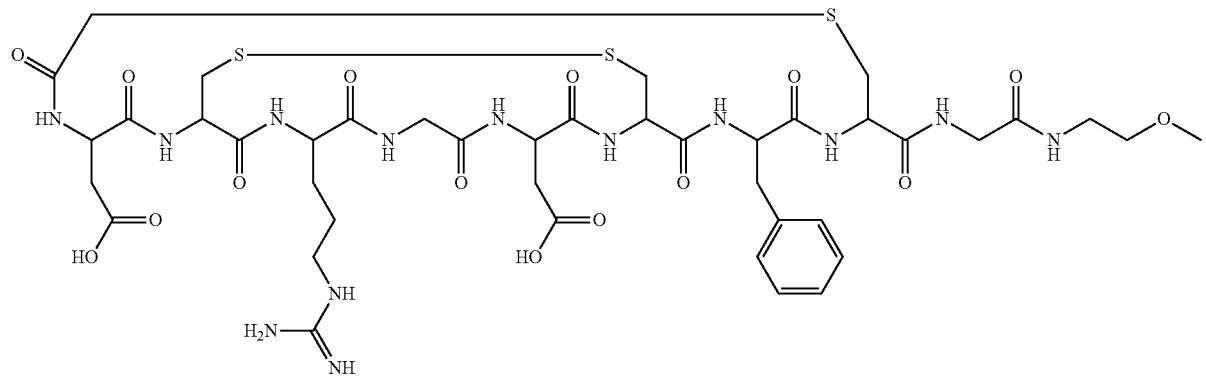
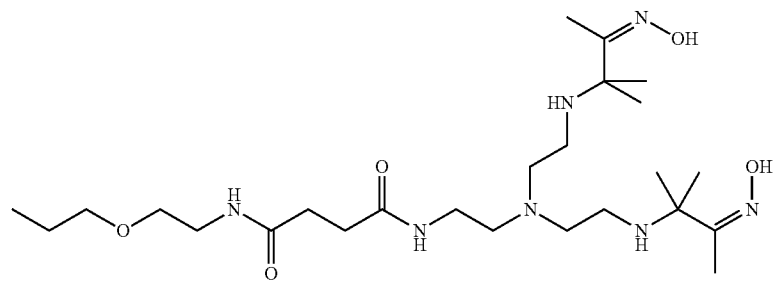
Compound VI
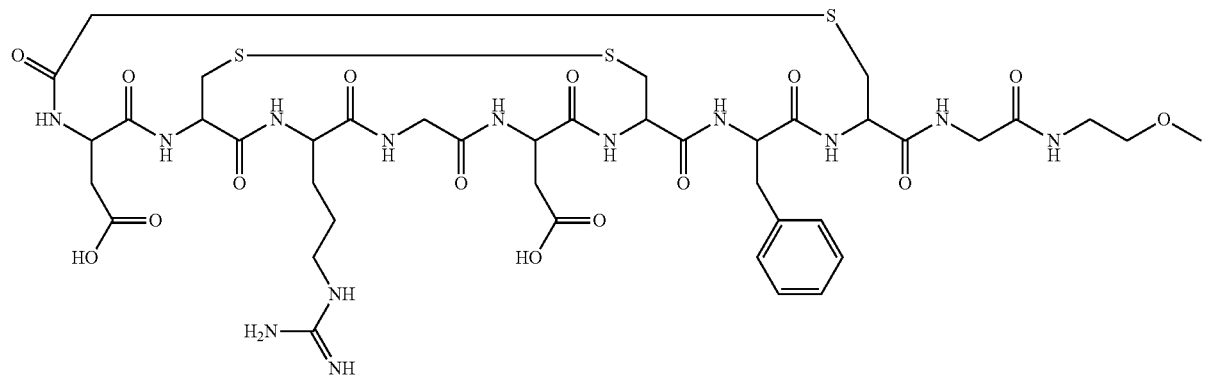
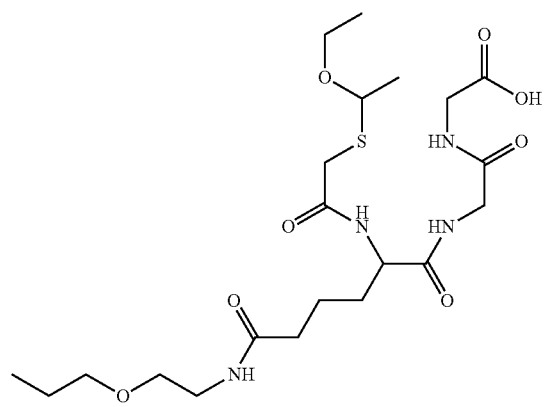

-continued
Compound VII
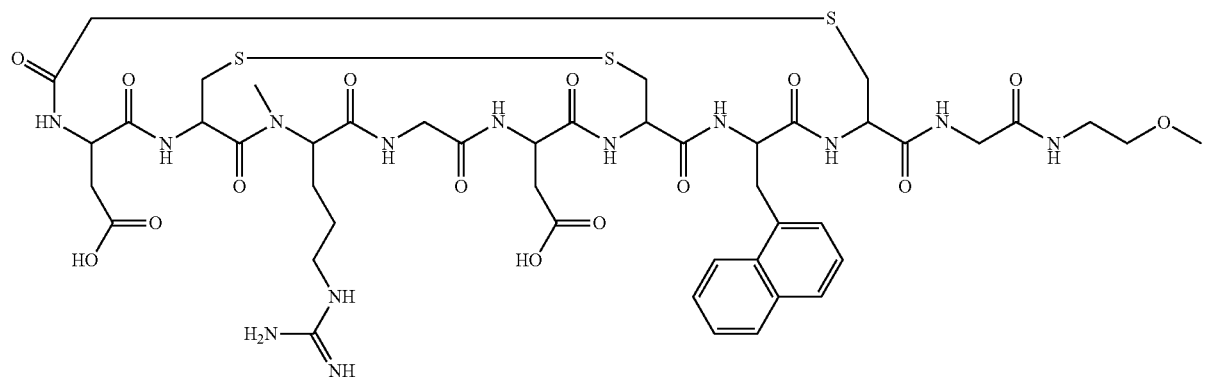
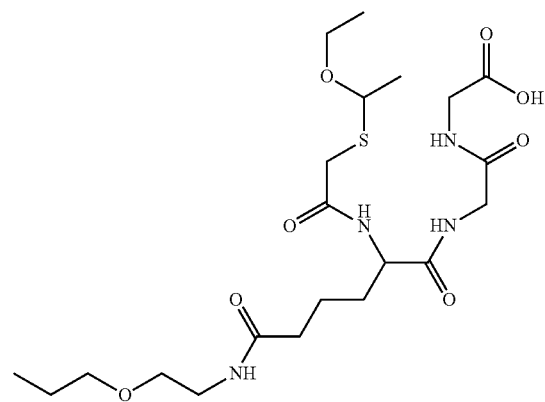
Compound VII
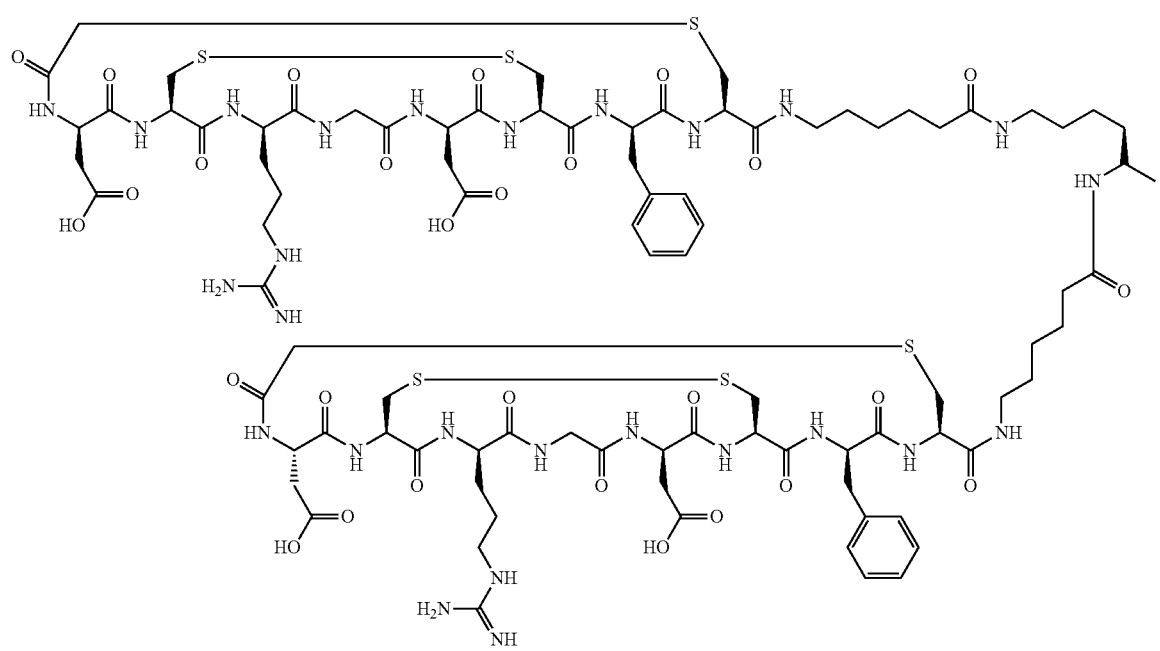

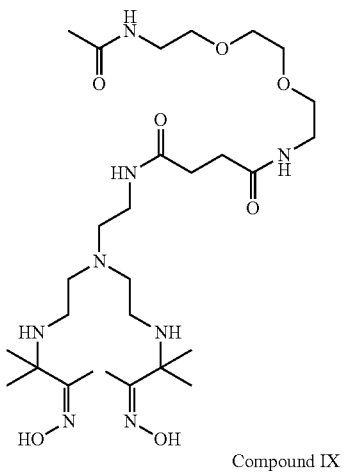

Compound IX

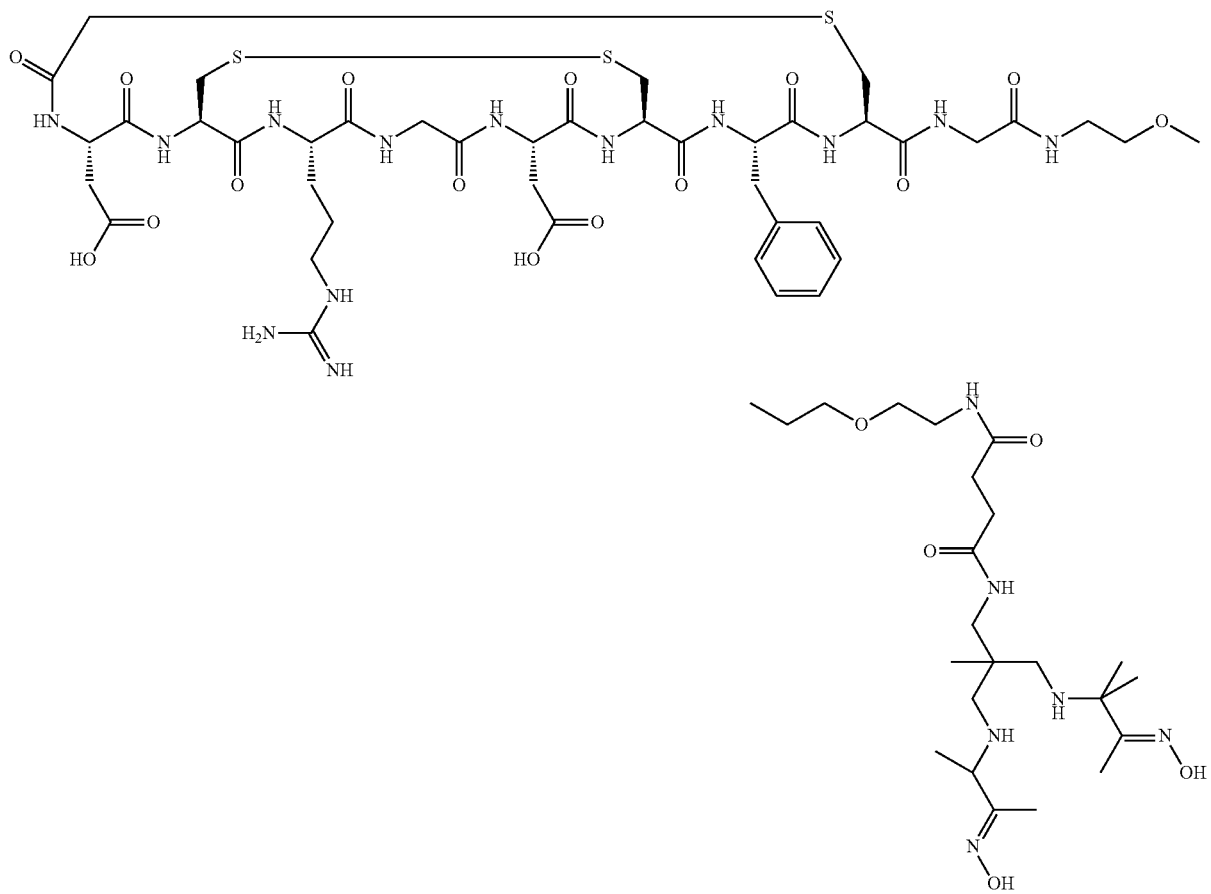

where Compound V and Compound VI are suitable for technetium labelling, Compound II may be labelled with a radioisotope of iodine and Compound III carries a tyrosine residue suitable for labelling with a radioisotope of iodine. Compound VII comprises a vector-chelate conjugate where the arginine and phenylalanine residues are replaced with N-methylarginine and naphthylalanine respectively increasing the enzymatic stability of the vector component. Compound IV comprises tyrosine instead of phenylalanine for radiolabelling with iodine, the C-terminal glycine has been removed and the acid function replaced by an amide bond to reduce vector degradation by carboxypeptidases.

The formula I as defined comprises one or multiple vectors (V)

wherein $X_1$ represents a bond or 1, 2, 3, 4 or 5 amino acid residues wherein each amino acid residue independently is optionally derivatized with a functional side-chain suitable for modifying the pharmacokinetics or blood clearance rates of the said agents, and $X_{2-6}$ are as defined by formula I, and $X_7$ represents 1, 2, 3, 4, 5, 6, 7, 8, 9 or 10 amino acid residues or is absent, and $X_8$ is absent.

In most cases, it is preferred that the amino-acids in the vector V are in the L-form. However, in some embodiments of the invention one, two, three or more of the amino-acids in the vector V are preferably in the D-form. The inclusion of such D-form amino-acids can have a significant effect on the serum stability of the vector. Reference is particularly made in this regard to vectors having D-tyrosine at position $X_1$.

According to the present invention, any of the amino acid residues as defined in formula I may preferably represent a naturally occurring amino acid and independently in any of the D or L conformations.

Compounds II-VII preferably have the stereo-specific conformations shown below:

Compound IIa

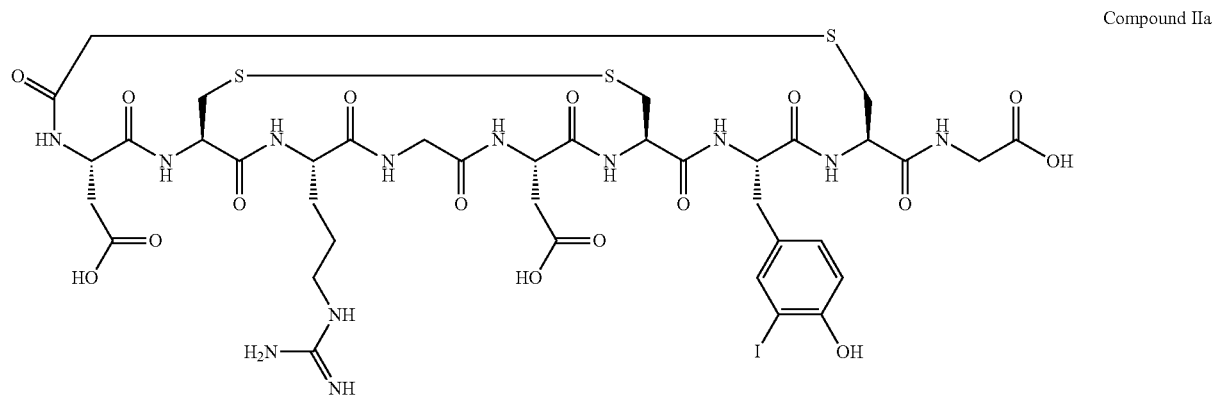

Compound IIIa

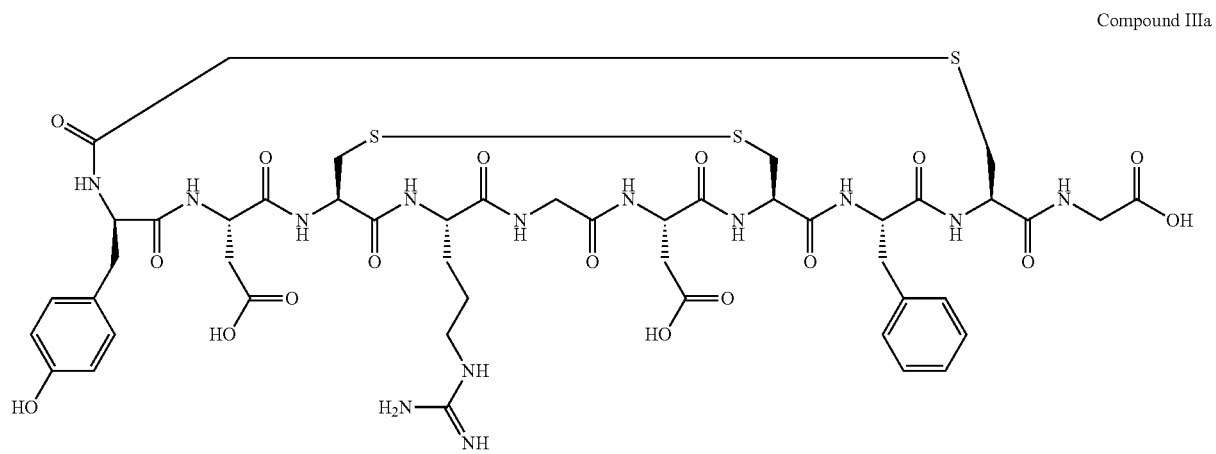

Compound IVa

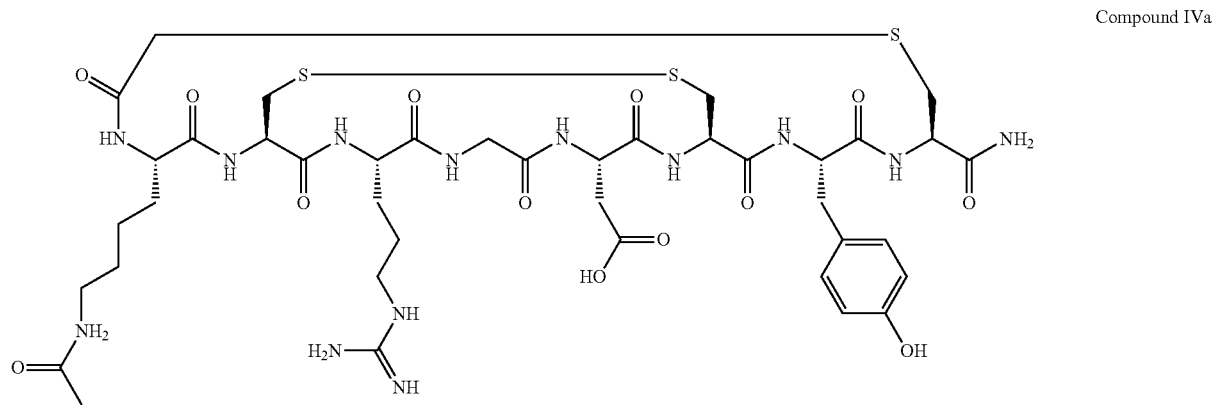

Compound Va
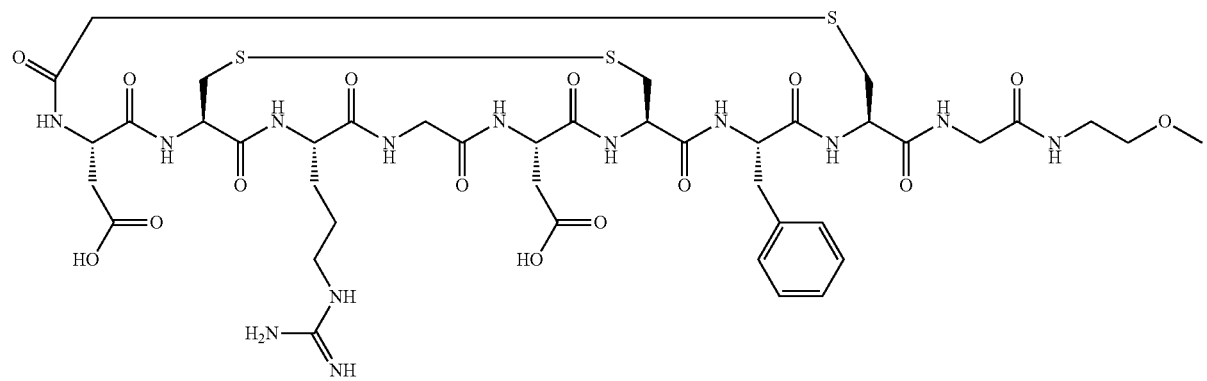
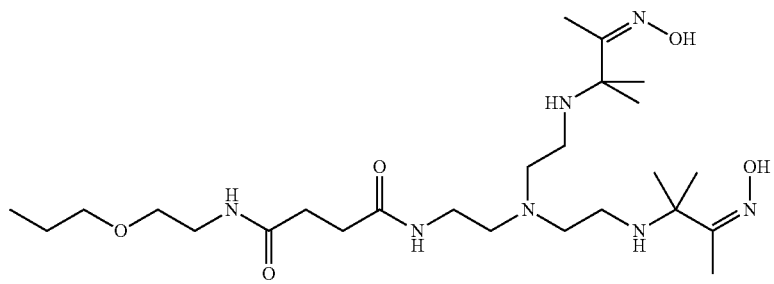
Molecular Weight = 1569.856
Exact Mass = 1568.690
Molecular Formula = C64H104N20O20S3
Compound VIa
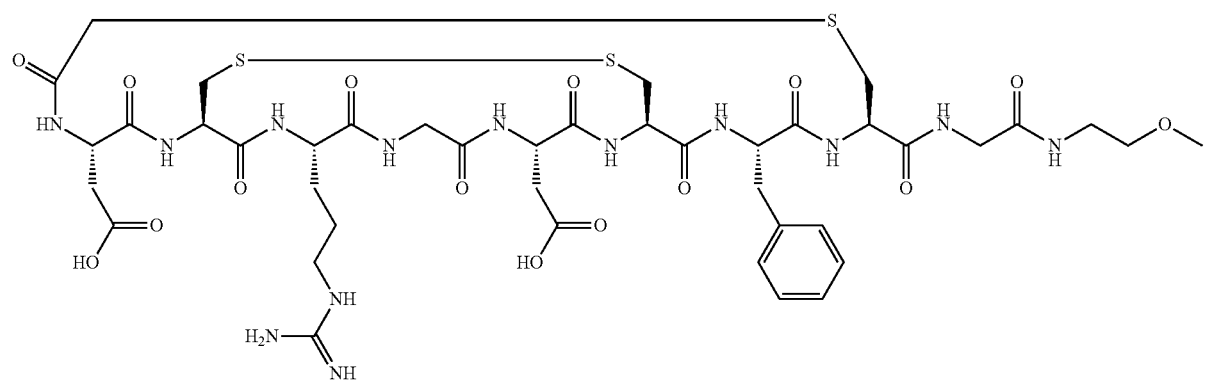
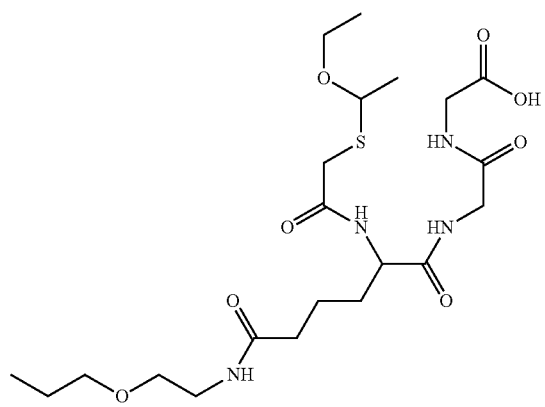

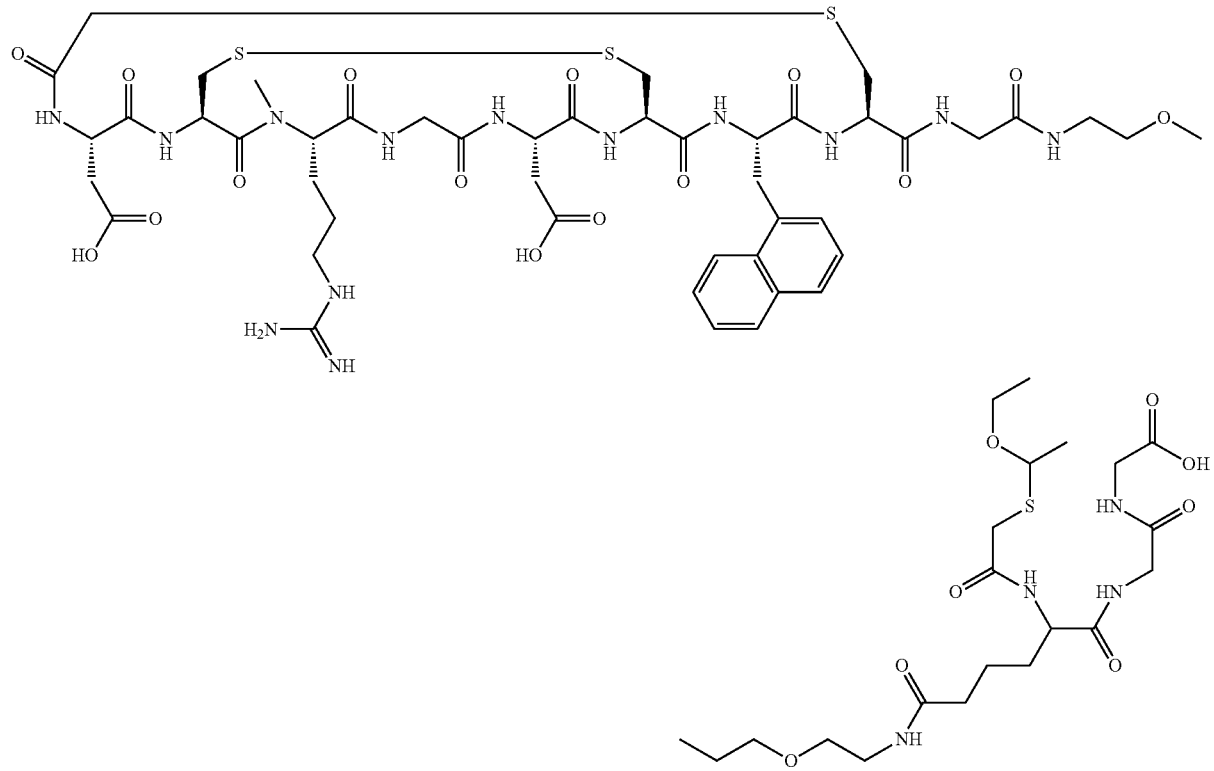

Compound VIIa

Some of the compounds of the invention are high affinity RGD based vectors. As used herein the term 'high affinity RGD based vector' refers to compounds that have a Ki of <100 nM, preferably <10 nM and most preferably <5 nM, in a competitive binding assay for αvβ3 integrin and where the Ki value was determined by competition with the known high affinity ligand echistatin. Methods for carrying out such competition assays are well known in the art.

The invention also provides a pharmaceutical composition comprising an effective amount (e.g. an amount effective for enhancing image contrast in in vivo imaging) of a compound of general formula I or a salt thereof, together with one or more pharmaceutically acceptable adjuvants, excipients or diluents.

The invention further provides a pharmaceutical composition for treatment of a disease comprising an effective amount of a compound of general formula I, or an acid addition salt thereof, together with one or more pharmaceutically acceptable adjuvants, excipients or diluents.

As mentioned above, the compounds of formula I may comprise vector, linker and reporter moieties. A linker moiety may serve to link one vector to one reporter; alternatively it may link together more than one vector and/or more than one reporter. Likewise a reporter or a vector may be linked to more than one linker. Use in this way of a plurality of reporters (e.g. several linker-reporter moieties attached to one vector or several reporters attached to one linker itself attached to one vector) may enable the detectability of the contrast agent to be increased (e.g. by increasing its radioopacity, echogenicity or relaxivity) or may enable it to be detected in more than one imaging modality. Use in this way of a plurality of vectors may e.g. increase the targeting efficiency of an contrast agent or may make the contrast agent/therapeutic agent able to target more than one site, e.g. different receptors for an agent which has receptor heterogeneity.

A wide variety of linkers can be used, including biodegradable linkers and biopolymers.

The linker component of the contrast agent is at its simplest a bond between the vector and reporter moieties. More generally however the linker will provide a mono- or multimolecular skeleton covalently or non-covalently linking one or more vectors to one or more reporters, e.g. a linear, cyclic, branched or reticulate molecular skeleton, or a molecular aggregate, with in-built or pendant groups which bind covalently or non-covalently, e.g. coordinatively, with the vector and reporter moieties or which encapsulate, entrap or anchor such moieties. One preferred embodiment of the invention provides compounds of formula I wherein one or multiple amino acids are a part of any individual linker component.

Thus linking of a reporter unit to a desired vector may be achieved by covalent or non-covalent means, usually involving interaction with one or more functional groups located on the reporter and/or vector. Examples of chemically reactive functional groups which may be employed for this purpose include amino, hydroxyl, sulfhydryl, carboxyl, and carbonyl groups, as well as carbohydrate groups, vicinal diols, thioethers, 2-aminoalcohols, 2-aminothiols, guanidinyl, imidazolyl and phenolic groups.

Covalent coupling of reporter and vector may therefore be effected using linking agents containing reactive moities capable of reaction with such functional groups.

It will be appreciated that functional groups in the reporter and/or vector may if desired be converted to other functional groups prior to reaction, e.g. to confer additional reactivity or selectivity.

A vector which is coupled to a peptide, lipooligosaccharide or lipopeptide linker which contains a element capable of mediating membrane insertion may also be useful.

So-called zero-length linking agents, which induce direct covalent joining of two reactive chemical groups without introducing additional linking material (e.g. as in amide bond formation induced using carbodiimides or enzymatically) may, if desired, be used in accordance with the invention, as may agents such as biotin/avidin systems which induce non-covalent reporter-vector linking and agents which induce electrostatic interactions.

Most commonly, however, the linking agent will comprise two or more reactive moieties, e.g. as described above, connected by a spacer element. The presence of such a spacer permits bifunctional linkers to react with specific functional groups within a molecule or between two different molecules, resulting in a bond between these two components and introducing extrinsic linker-derived material into the reporter-vector conjugate. The reactive moieties in a linking agent may be the same (homobifunctional agents) or different (heterobifunctional agents or, where several dissimilar reactive moieties are present, heteromultifunctional agents), providing a diversity of potential reagents that may bring about covalent bonding between any chemical species, either intramolecularly or intermolecularly.

The nature of extrinsic material introduced by the linking agent may have a critical bearing on the targeting ability and general stability of the ultimate product. Thus it may be desirable to introduce labile linkages, e.g. containing spacer arms which are biodegradable or chemically sensitive or which incorporate enzymatic cleavage sites.

Alternatively the spacer may include polymeric components, e.g. to act as surfactants and enhance the stability of the agent. The spacer may also contain reactive moieties, e.g. as described above to enhance surface crosslinking. Spacer elements may also comprise macromolecular structures such as dextran and preferably poly(ethyleneglycols), usually referred to as PEGs. In addition to spacer elements, PEGs may also be used to modify the in vivo characteristics of the vectors.

Other representative spacer elements include structural-type polysaccharides, storage-type polysaccharides, polyamino acids and methyl and ethyl esters thereof, and polypeptides, oligosaccharides and oligonucleotides, which may or may not contain enzyme cleavage sites.

Preferred linking groups are derived from vector reactive groups selected from but not limited to:— a group that will react directly with carboxy, aldehyde, amine (NHR), alcohols, sulfhydryl groups, activated methylenes and the like, on the vector, for example, active halogen containing groups, a group that can react readily with modified vector molecules containing a vector reactive group, i.e., vectors containing a reactive group modified to contain reactive groups, for example, by oxidation of the vector to an aldehyde or a carboxylic acid, and a group that can be linked to the vector containing a reactive group, or to the modified vector as noted above by use of a crosslinking agent.

Preferred useful linking groups are derived from various heterobifunctional cross-linking reagents such as those listed in the Pierce Chemical Company Immunotechnology Catalog—Protein Modification Section, (1995 and 1996).

In addition to the foregoing description, the linking groups, in whole or in part, can also be comprised of and derived from complementary sequences of nucleotides and residues of nucleotides, both naturally occurring and modified, preferably non-self-associating oligonucleotide sequences.

Linking agents used in accordance with the invention will in general bring about linking of vector to reporter or reporter to reporter with some degree of specificity, and may also be used to attach one or more therapeutically active agents.

Further examples of the linkers which may be used in the context of the current application are given on pages 32-54 of WO98/47541 and the disclosures made on these pages are incorporated herein by reference in their entirety. It is hereby asserted that each and every linker or part thereof disclosed on the aforementioned pages is considered to be part of the description of the invention contained in this application.

The reporter moieties in the contrast agents of the invention may be any moiety capable of detection either directly or indirectly in an in vivo diagnostic imaging procedure. Preferably the contrast agent comprises one reporter. Preferred moieties are moieties which emit or may be caused to emit detectable radiation (e.g. by radioactive decay, fluorescence excitation, spin resonance excitation, etc.), moieties which affect local electromagnetic fields (e.g. paramagnetic, superparamagnetic, ferrimagnetic or ferromagnetic species), moieties which absorb or scatter radiation energy (e.g. chromophores and fluorophores), particles (including liquid containing vesicles), heavy elements and compounds thereof, and moieties which generate a detectable substance, etc.

A very wide range of materials detectable by diagnostic imaging modalities is known from the art and the reporter will be selected according to the imaging modality to be used. Thus for example for ultrasound imaging an echogenic material, or a material capable of generating an echogenic material will normally be selected. The vectors may be coupled via a linker to a suitable lipid reporter/carrier for incorporation into a gas-filled microbubble. Such microbubbles may be used for targeting ultrasound imaging. For X-ray imaging the reporter will generally be or contain a heavy atom (e.g. of atomic weight 38 or above); for MR imaging the reporter will either be a non zero nuclear spin isotope (such as $^{19}$F) or a material having unpaired electron spins and hence paramagnetic, superparamagnetic, ferrimagnetic or ferromagnetic properties; for light imaging the reporter will be a light scatterer (e.g. a coloured or uncoloured particle), a light absorber or a light emitter; for magnetometric imaging the reporter will have detectable magnetic properties; for electrical impedance imaging the reporter will affect electrical impedance; and for scintigraphy, SPECT, PET, etc., the reporter will be a radionuclide.

Examples of suitable reporters are widely known from the diagnostic imaging literature, e.g. magnetic iron oxide particles, X-ray contrast agent containing vesicles, chelated paramagnetic metals (such as Gd, Dy, Mn, Fe etc.).

Stated generally, the reporter may be (1) a chelatable metal or polyatomic metal-containing ion (i.e. TcO, etc), where the metal is a high atomic number metal (e.g. atomic number greater than 37), a paramagnetic species (e.g. a transition metal or lanthanide), or a radioactive isotope, (2) a covalently bound non-metal species which is an unpaired electron site (e.g. an oxygen or carbon in a persistant free radical), a high atomic number non-metal, or a radioisotope, (3) a polyatomic cluster or crystal containing high atomic number atoms, displaying cooperative magnetic behaviour (e.g. superparamagnetism, ferrimagnetism or ferromagnetism) or containing radionuclides, (4) a chromophore (by which term species which are fluorescent or phosphorescent are included), e.g. an inorganic or organic structure, particularly a complexed metal ion or an organic group having an extensive delocalized electron system, or (5) a structure or group having electrical impedance varying characteristics, e.g. by virtue of an extensive delocalized electron system.

Examples of particular preferred reporter groups are described in more detail below.

Chelated metal reporters are preferably chosen from the group of metal radionuclides, paramagnetic metal ions, fluorescent metal ions, heavy metal ions and cluster ions.

Preferred metal radionuclides include $^{90}Y$, $^{99m}Tc$, $^{111}In$, $^{47}Sc$, $^{67}Ga$, $^{51}Cr$, $^{177m}Sn$, $^{67}Cu$, $^{167}Tm$, $^{97}Ru$, $^{188}Re$, $^{177}Lu$, $^{199}Au$, $^{203}Pb$ and $^{141}Ce$.

Preferred paramagnetic metal ions include ions of transition and lanthanide metals (e.g. metals having atomic numbers of 6 to 9, 21-29, 42, 43, 44, or 57-71), in particular ions of Cr, V, Mn, Fe, Co, Ni, Cu, La, Ce, Pr, Nd, Pm, Sm, Eu, Gd, Tb, Dy, Ho, Er, Tm, Yb and Lu, especially of Mn, Cr, Fe, Gd and Dy, more especially Gd.

The metal ions are desirably chelated by chelant groups on the linker moiety or in or on a particle, (e.g. a vesicle or a porous or non-porous inorganic or organic solid), in particular linear, macrocyclic, terpyridine and $N_2S_2$ chelants, such as for example DTPA, DTPA-BMA, EDTA, D03A and TMT. Further examples of suitable chelant groups are disclosed in U.S. Pat. No. 4,647,447, WO89/00557, U.S. Pat. No. 5,367,080, U.S. Pat. No. 5,364,613, etc.

The linker moiety or the particle may contain one or more such chelant groups, if desired metallated by more than one metal species (e.g. so as to provide reporters detectable in different imaging modalities).

Methods for metallating any chelating agents present are within the level of skill in the art. Metals can be incorporated into a chelant moiety by any one of three general methods: direct incorporation, template synthesis and/or transmetallation. Direct incorporation is preferred.

Thus it is desirable that the metal ion be easily complexed to the chelating agent, for example, by merely exposing or mixing an aqueous solution of the chelating agent-containing moiety with a metal salt in an aqueous solution preferably having a pH in the range of about 4 to about 11. The salt can be any salt, but preferably the salt is a water soluble salt of the metal such as a halogen salt, and more preferably such salts are selected so as not to interfere with the binding of the metal ion with the chelating agent. The chelating agent-containing moiety is preferably in aqueous solution at a pH of between about 5 and about 9, more preferably between pH about 6 to about 8. The chelating agent-containing moiety can be mixed with buffer salts such as citrate, acetate, phosphate and borate to produce the optimum pH. Preferably, the buffer salts are selected so as not to interfere with the subsequent binding of the metal ion to the chelating agent.

In diagnostic imaging, the vector-linker-reporter $(V)_kLR$ construct preferably contains a ratio of metal radionuclide ion to chelating agent that is effective in such diagnostic imaging applications. In preferred embodiments, the mole ratio of metal ion per chelating agent is from about 1:1,000 to about 1:1.

In radiotherapeutic applications, the $(V)_kLR$ preferably contains a ratio of metal radionuclide ion to chelating agent that is effective in such therapeutic applications. In preferred embodiments, the mole ratio of metal ion per chelating agent is from about 1:100 to about 1:1. The radionuclide can be selected, for example, from radioisotopes of Sc, Fe, Pb, Ga, Y, Bi, Mn, Cu, Cr, Zn, Ge, Mo, Ru, Sn, Sr, Sm, Lu, Sb, W, Re, Po, Ta and Tl. Preferred radionuclides include $^{44}Sc$, $^{64}Cu$, $^{67}Cu$, $^{212}Pb$, $^{68}Ga$, $^{90}Y$, $^{153}Sm$, $^{212}Bi$, $^{186}Re$ and $^{188}Re$. Of these, especially preferred is $^{90}Y$. These radioisotopes can be atomic or preferably ionic.

The following isotopes or isotope pairs can be used for both imaging and therapy without having to change the radiolabeling methodology or chelator: $^{47}Sc_{21}$; $^{141}Ce_{58}$; $^{188}Re_{75}$; $^{177}Lu_{71}$; $^{199}Au_{79}$; $^{47}Sc_{21}$; $^{131}I_{53}$; $^{67}Cu_{29}$; $^{131}I_{53}$ and $^{123}I_{53}$; $^{188}Re_{75}$ and $^{99m}Tc_{43}$; $^{90}Y_{39}$ and $^{87}Y_{39}$; $^{47}Sc_{21}$ and $^{44}Sc_{21}$; $^{90}Y_{39}$ and $^{123}I_{53}$; $^{146}Sm_{62}$ and $^{153}Sm_{62}$; and $^{90}Y_{39}$ and $^{111}In_{49}$.

The chelant moieties may be attached via backbone functionalization of the chelant or by utilization of one or more of the metal co-ordinating groups of the chelant or by amide or ether bond formation between acid chelant and an amine or hydroxyl carrying linker backbone, e.g. as in polylysine-polyDTPA, polylysine-polyDOTA and in the so-called magnifier polychelants, of PCT/EP96/00565. Such moieties may be conjugated to one or more vector groups either directly (e.g. utilizing amine, acid or hydroxyl groups in the polychelant linker) or via a bifunctional linker compound as discussed above for monochelant linkers.

Where the chelated species is carried by a particulate (or molecular aggregate, e.g. vesicular) linker, the chelate may for example be an unattached mono or polychelate (such as Gd DTPA-BMA or Gd HP-DO3A) enclosed within the particle or it may be a mono or polychelate conjugated to the particle either by covalent bonding or by interaction of an anchor group (e.g. a lipophilic group) on the mono/polychelate with the membrane of a vesicle (see for example PCT/GB95/02378).

Preferred non-metal atomic reporters include radioisotopes such as $^{123}I$, $^{131}I$ and $^{18}F$ as well as non zero nuclear spin atoms such as $^{19}F$, and heavy atoms such as I.

Such reporters, preferably a plurality thereof, e.g. 2 to 200, may be covalently bonded to a linker backbone, either directly using conventional chemical synthesis techniques or via a supporting group, e.g. a triiodophenyl group.

In an embodiment of this invention, the use of radioisotopes of iodine or fluorine is specifically contemplated. For example, if the vector or linker is comprised of substituents that can be chemically substituted by iodine or fluorine in a covalent bond forming reaction, such as, for example, substituents containing hydroxyphenyl or p-nitrobenzoyl functionality, such substituents can be labeled by methods well known in the art with a radioisotope of iodine or fluorine respectively. These species can be used in therapeutic and diagnostic imaging applications. While, at the same time, a metal attached to a chelating agent on the same vector-linker can also be used in either therapeutic or diagnostic imaging applications.

As with the metal chelants discussed above, such metal atomic reporters may be linked to the linker or carried in or on a particulate linker, e.g. in a vesicle (see WO95/26205 and GB 9624918.0).

Linkers of the type described above in connection with the metal reporters may be used for non-metal atomic reporters with the non-metal atomic reporter or groups carrying such reporters taking the place of some or all of the chelant groups.

Preferably the $(V)_kLR$ agents of the invention will have the receptor targeting vectors coupled directly or indirectly to a reporter, e.g. with covalently bound iodine radioisotopes, with metal chelates attached directly or via an organic linker group or coupled to a particulate reporter or linker-reporter, e.g. a superparamagnetic crystals (optionally coated, e.g. as in PCT/GB97/00067), or a vesicle, e.g. an iodinated contrast agent containing micelle or liposome.

A preferred embodiment of the invention relates to a radio-labelled agent of general formula (I), particularly for use in tumour imaging.

The diagnostic agents of the invention may be administered to patients for imaging in amounts sufficient to yield the desired contrast with the particular imaging technique. Where the reporter is a metal, generally dosages of from 0.001 to 5.0 mmoles of chelated imaging metal ion per kilogram of patient bodyweight are effective to achieve adequate contrast enhancements. Where the reporter is a radionuclide, dosages of 0.01 to 100 mCi, preferably 0.1 to 50 mCi will normally be sufficient per 70 kg bodyweight.

The dosage of the compounds of the invention for therapeutic use will depend upon the condition being treated, but in general will be of the order of from 1 pmol/kg to 1 mmol/kg bodyweight.

The compounds according to the invention may therefore be formulated for administration using physiologically acceptable carriers or excipients in a manner fully within the skill of the art. For example, the compounds, optionally with the addition of pharmaceutically acceptable excipients, may be suspended or dissolved in an aqueous medium, with the resulting solution or suspension then being sterilized.

The compounds of formula I may be therapeutically effective in the treatment of disease states as well as detectable in in vivo imaging. Thus for example the vector on the reporter moieties may have therapeutic efficacy, e.g. by virtue of the radiotherapeutic effect of a radionuclide reporter, the efficacy in photodynamic therapy of a chromophore (or fluorophore) reporter or the chemotherapeutic effect of the vector moiety.

Use of the compounds of formula I in the manufacture of therapeutic compositions (medicament) and in methods of therapeutic or prophylactic treatment, preferably treatment of cancer, of the human or non-human animal body are thus considered to represent further aspects of the invention.

Further examples of the reporters which may be used in the context of the current application are given on pages 63-66 and 70-86 of WO98/47541 and the disclosures made on these pages are incorporated herein by reference in their entirety. It is hereby asserted that each and every reporter or part thereof disclosed on the aforementioned pages is considered to be part of the description of the invention contained in this application.

Viewed from a further aspect the invention provides the use of a compound of formula I for the manufacture of a contrast medium for use in a method of diagnosis involving administration of said contrast medium to an animate subject and generation of an image of at least part of said subject.

Viewed from a still further aspect the invention provides a method of generating an image of an animate human or non-human (preferably mammalian or avian) animal subject involving administering a contrast agent to said subject, e.g. into the vascular system and generating an image of at least a part of said subject to which said contrast agent has distributed, e.g. by X-ray, MR, ultrasound, scintigraphy, PET, SPECT, electrical impedance, light or magnetometric imaging modalities, wherein as said contrast agent is used an agent of formula I.

Viewed from a still further aspect the invention provides a method of generating enhanced images of a human or non-human animal subject previously administered with a contrast agent composition comprising a compound as defined by formula I, which method comprises generating an image of at least part of said subject.

Viewed from a further aspect the invention provides a method of monitoring the effect of treatment of a human or non-human animal subject with a drug to combat a condition associated with cancer, preferably angiogenesis, e.g. a cytotoxic agent, said method involving administering to said subject an agent of formula I and detecting the uptake of said agent by cell receptors, preferably endothelial cell receptors and in particular αvβ3 receptors, said administration and detection optionally but preferably being effected repeatedly, e.g. before, during and after treatment with said drug.

Viewed from a yet further aspect the invention provides a process for the preparation of an agent of formula I, said process comprising the conjugation of a vector V to a compound detectable in a diagnostic imaging procedure or a chelant compound and if necessary metallating chelant groups in the resultant conjugate with a metal ion detectable in a diagnostic imaging procedure.

The compounds of the present invention can be synthesised using all the known methods of chemical synthesis but particularly useful is the solid-phase methodology of Merrifield employing an automated peptide synthesiser (J. Am. Chem. Soc., 85: 2149 (1964)). Vectors containing multiple bridges are synthesised using differential cysteine protecting groups so that no ambiguity exists as to the final folded form of the vector. The peptides and peptide chelates may be purified using high performance liquid chromatography (HPLC) and characterised by mass spectrometry and analytical HPLC before testing in the in vitro screen.

The present invention will now be further illustrated by way of the following non-limiting examples.

EXAMPLE 1

Synthesis of Compound V1a 1 a) Synthesis of ClCH$_2$CONH-Asp-Cys(MBzl)-Arg-Gly-Asp-Cys(MBzl)-Phe-Cys-Gly-NH—(CH$_2$CH$_2$O)$_2$CH$_2$CH$_2$NH$_2$

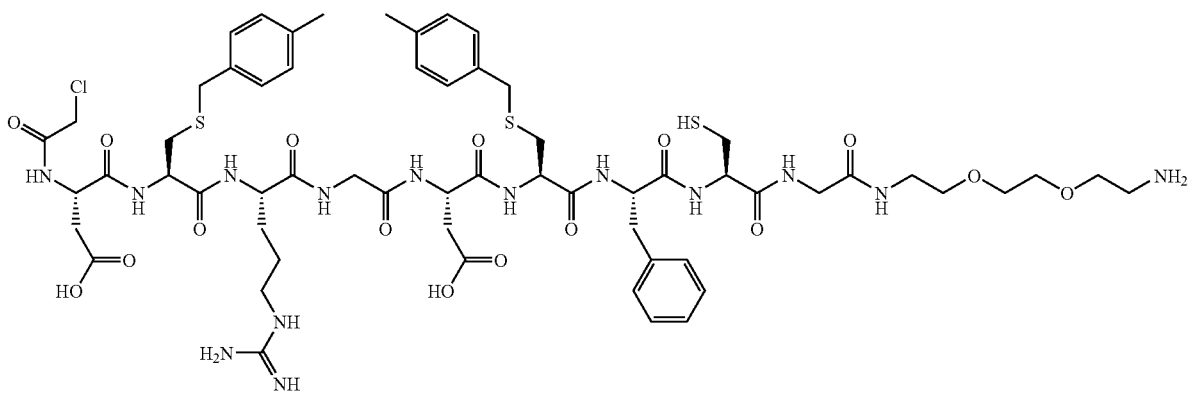

Exact Mass = 1388
Molecular Formula = C60H85ClN14O16S3

The peptide was synthesised on a ABI 433A automatic peptide synthesiser starting with O-Bis-(aminoethyl)ethylene glycol trityl resin on a 0.25 mmol scale using 1 mmol amino acid and chloroacetic acid cartridges. The amino acids and chloroacetic acid were pre-activated using HBTU before coupling. The simultaneous removal of peptide and side-chain protecting groups (except MBzl) from the resin was carried out in TFA containing TIS (5%), H$_2$O (5%) and phenol (2.5%) for two hours and twenty minutes.

After work-up 250 mg of crude peptide was obtained (Analytical HPLC: Gradient, 5-50% B over 20 min where A=H$_2$O/0.1% TFA and B=CH$_3$CN/0.1% TFA; column, VYDAC C18 218TP54; detection, UV 214 nm; product retention time, 20.55 min). Further product characterisation was carried out using MALDI mass spectrometry: expected, M+H at 1389, found, at 1392).

1 b) Synthesis of cyclo[-CH$_2$CONH-Asp-Cys(MBzl)-Arg-Gly-Asp-Cys(MBzl)-Phe-Cys]-Gly-NH—(CH$_2$CH$_2$O)$_2$CH$_2$CH$_2$NH$_2$ 250 mg of ClCH$_2$CONH-Asp-Cys (MBzl)-Arg-Gly-Asp-Cys (MBzl)-Phe-Cys-Gly-NH—(CH$_2$CH$_2$O)$_2$CH$_2$CH$_2$NH$_2$ was dissolved in water/acetonitrile. The mixture was adjusted to pH 8 with ammonia solution and stirred for 20 hours.

After lyophilisation 240 mg of crude peptide was obtained (Analytical HPLC: Gradient, 5-50% B over 20 min where A=H$_2$O/0.1% TFA and B=CH$_3$CN/0.1% TFA; column, VYDAC C18 218TP54; detection, UV 214 nm; product retention time, 19.45 min). Further product characterisation was carried out using MALDI mass spectrometry: expected, M+H at 1353, found, at 1358).

1 c) Synthesis of [Cys$^{2-6}$]cyclo[-CH$_2$CONH-Asp-Cys-Arg-Gly-Asp-Cys-Phe-Cys]-Gly-NH—(CH$_2$CH$_2$O)$_2$CH$_2$CH$_2$NH$_2$

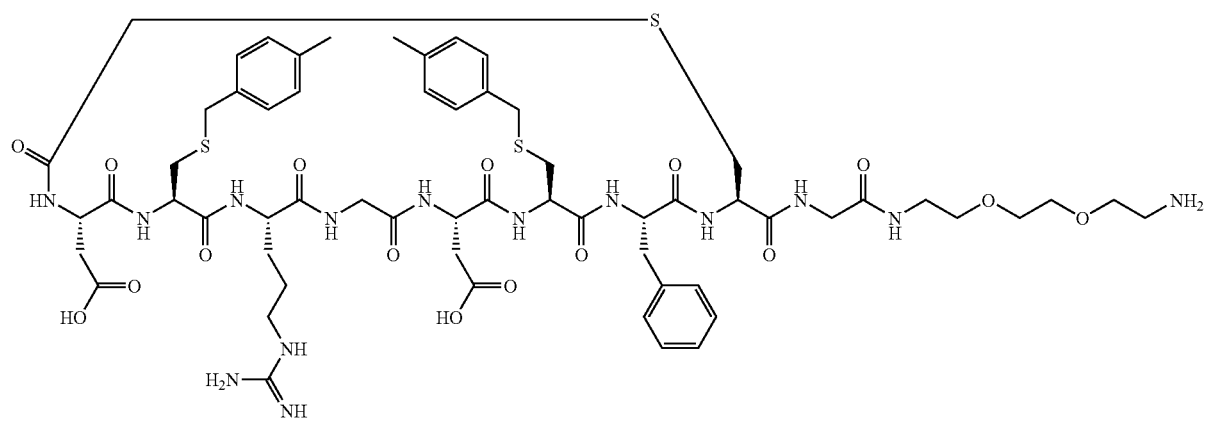

Exact Mass = 1352  Molecular Formula = C60H84N14O16S3

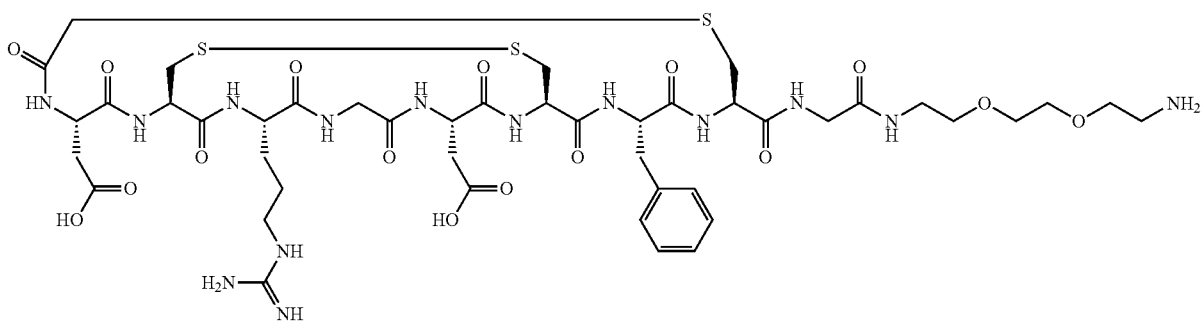

Molecular Weight = 1143.29
Exact Mass = 1142
Molecular Formula = C44H66N14O16S3

100 mg of cyclo[CH$_2$CONH-Asp-Cys (MBzl)-Arg-Gly-Asp-Cys (MBzl)-Phe-Cys]-Gly-NH—(CH$_2$CH$_2$O)$_2$CH$_2$CH$_2$NH$_2$ was dissolved in TFA (10 ml) then added to a preheated solution of anisole (200 µl), DMSO (5 ml) and TFA (90 ml). The mixture was stirred at 60° C. for 60 min following which the TFA was removed in vacuo and the peptide precipitated by the addition of diethyl ether.

Purification by preparative HPLC (Vydac C18 218TP1022 column) of the crude material was carried out using 0-30% B, where A=H$_2$O/0.1% TFA and B=CH$_3$CN/0.1% TFA, over 40 min at a flow rate of 9 mL/min. After lyophilization 26 mg of pure material was obtained (Analytical HPLC: Gradient, 0-35% B where A=H$_2$O/0.1% TFA and B=CH$_3$CN/0.1% TFA; column, VYDAC C18 218TP54; detection, UV 214 nm; product retention time, 14.33 min). Further product characterisation was carried out using MALDI mass spectrometry: expected, M+H at 1143, found, at 1148).

1 d) Conjugation of [Cys$^{2-6}$]cyclo[CH$_2$CONH-Asp-Cys-Arg-Gly-Asp-Cys-Phe-Cys]-Gly-NH—(CH$_2$CH$_2$O)$_2$CH$_2$CH$_2$NH$_2$ with N$_3$S-adipate chelate—Compound V1a:

5-50% B over 10 min where A=H$_2$O/0.1% TFA and B=CH$_3$CN/0.1% TFA; column, Phenomenex Luna 3µ C18 (2) 50×4.6 mm; detection, UV 214 nm; product retention time, 6.55 min). Further product characterisation was carried out using MALDI mass spectrometry: expected, M+H at 1150, found, at 1546).

1 e) Technetium Labelling of Compound V1a.

In a nitrogen filled vial was added Compound V1a (50 µg) dissolved in water (50 µL), 150 µL of sodium gluconate solution (25 mg in 6 mL H$_2$O), 100 µL ammonium acetate (pH 4.0, 50 mM), 1 mL TcO$_4$ soln (500 MBq) and 50 µL SnCl$_2$ soln (20 mg in 100 mL H$_2$0). The mixture was heated at 75° C. for 20 minutes before analysis by ITLC and HPLC.

EXAMPLE 2

Conjugation of [Cys$^{2-6}$]cyclo[CH$_2$CONH-Asp-Cys-Arg-Gly-Asp-Cys-Phe-Cys]-Gly-NH(CH$_2$CH$_2$O)$_2$CH$_2$CH$_2$NH$_2$ with Pn216 Chelate (Compound Va)

2 a) Synthesis of Pn216 Chelate

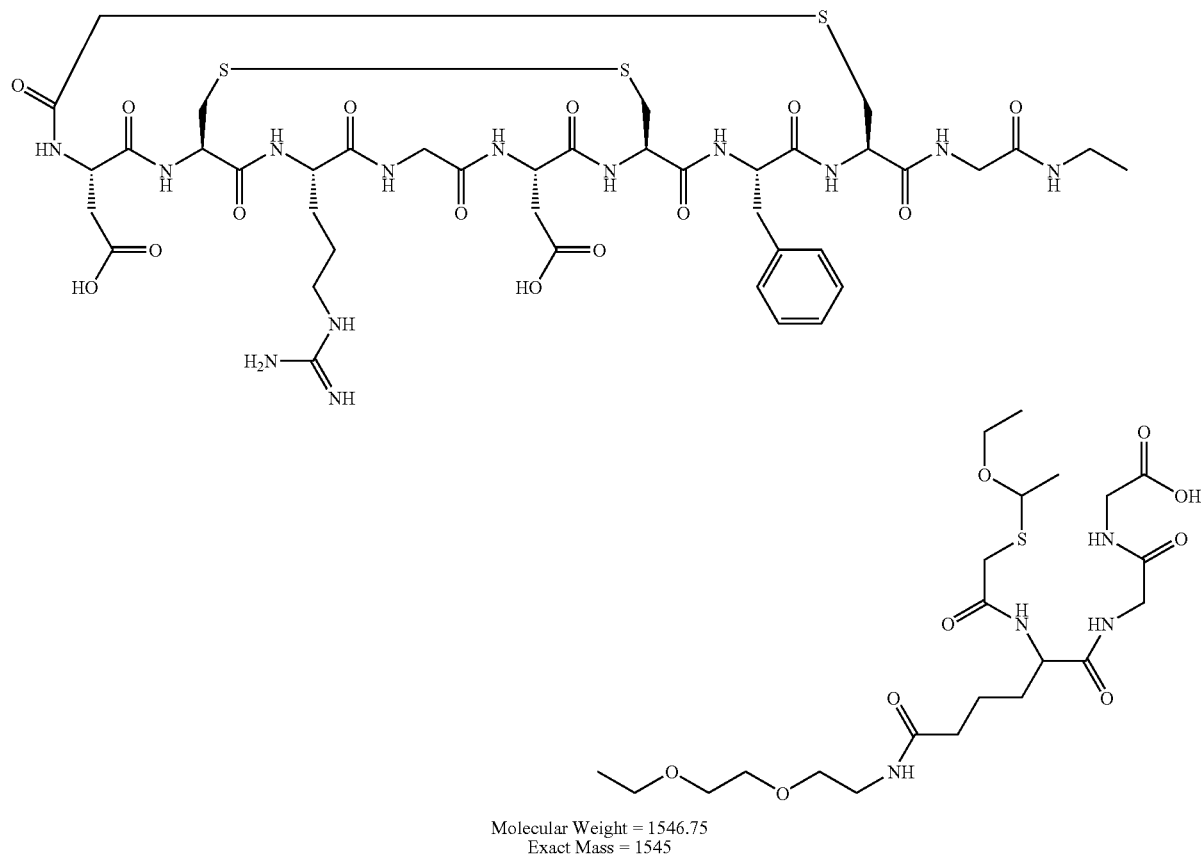

Molecular Weight = 1546.75
Exact Mass = 1545
Molecular Formula = C60H91N17O23S4

6.5 mg of N$_3$S-Adipate chelator active ester dissolved in acetonitrile (5 ml) was added to 5.1 mg of [Cys$^{2-6}$]cyclo[CH$_2$CONH-Asp-Cys-Arg-Gly-Asp-Cys-Phe-Cys]-Gly-NH—(CH$_2$CH$_2$O)$_2$CH$_2$CH$_2$NH$_2$ dissolved in DPBS (5 ml, pH 7.4). The mixture was stirred for 3 days.

Purification by preparative HPLC (Vydac C18 218TP1022 column) of the reaction mixture was carried out using 5-30% B, where A=H$_2$O/0.1% TFA and B=CH$_3$CN/0.1% TFA, over 40 min at a flow rate of 9 mL/min. After lyophilization 4.3 mg of pure material was obtained (Analytical HPLC: Gradient, Chloro-Nitroso Intermediate (3-chloro-3-methyl-2-nitrosobutane)

A mixture of 2-methylbut-2-ene (18.5 mL) and iso-amyl nitrate (19.5 mL) was stirred, cooled to −10° C. and concentrated hydrochloric acid (17.5 mL) added carefully to maintain the temperature below 0° C. The reaction was stirred at this temperature for 30 minutes. The precipitate formed was collected by filtration, washed 4×5 mL of ethanol (−20° C.) and dried in vacuo to give 3-chloro-3-methyl-2-nitrosobutane as a white solid.

2 b) Pn216-(3,3,11,11-tetramethyl-7-aminoethyl-4,7,10,triazamidecane-2,12-dionedioxime)

To a solution of tris-(2-aminoethyl)amine in acetonitrile (20 mL) was added sodium bicarbonate (2.2 g, 26 mmol). A solution of 3-chloro-3-methyl-2-nitrosobutane (1.8 g, 13 mmol) in dry acetonitrile was added slowly at 0° C. The reaction mixture was left to stir at room temperature for 4 hours and then filtered. The filtrant was washed with acetonitrile and the filtrate evaporated. The crude product was dissolved in acetonitrile and purified by HPLC to afford Pn216. Yield 0.88 g, 19%

2 c) Synthesis of Pn216-Succinic Acid Intermediate:

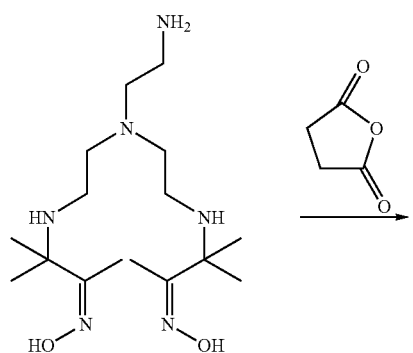

Succinic anhydride (100)
Pn216 (358)
Tetrafluorothiophenol (182)
DCCI (206)

Pn216 (0.5 g, 1.4 mmol) was dissolved in DMF (5 mL) and succinic anhydride (0.015 g, 1.5 mmol) in DMF (10 mL) added portionwise with stirring. The reaction was left stirring for 16 hours to afford complete conversion to the desired product. The pure acid was obtained following HPLC chromatography in good yield.

2 d) Synthesis of the Tetrafluorothiophenol Ester Derivative of Pn216-Succinic Acid

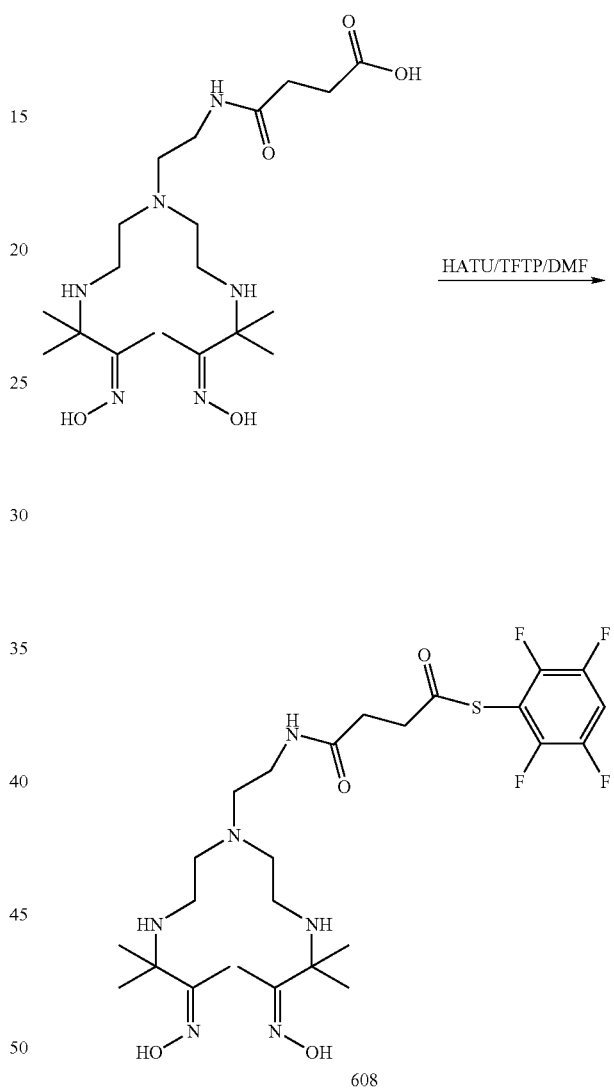

To Pn216 acid (10 mg, 0.022 mmol) in DMF (1.0 mL) was added HATU (8.3 mg, 0.022 mmol) and NMM (0.007 mL, 0.066 mmol). The mixture was stirred for 5 minutes then TFTP (0.022 mmol, 4 mg) added. The solution was stirred for 30 minutes then the reaction mixture was diluted with 20% acetonitrile/$H_2O$ (3 mL) and the product purified by reverse-phase chromatography yielding 6 mg of the desired product following freeze-drying.

2 e): For Synthesis of Peptide, See Example 1a) to c)
2 f) Conjugation of Peptide and Pn216 Chelate

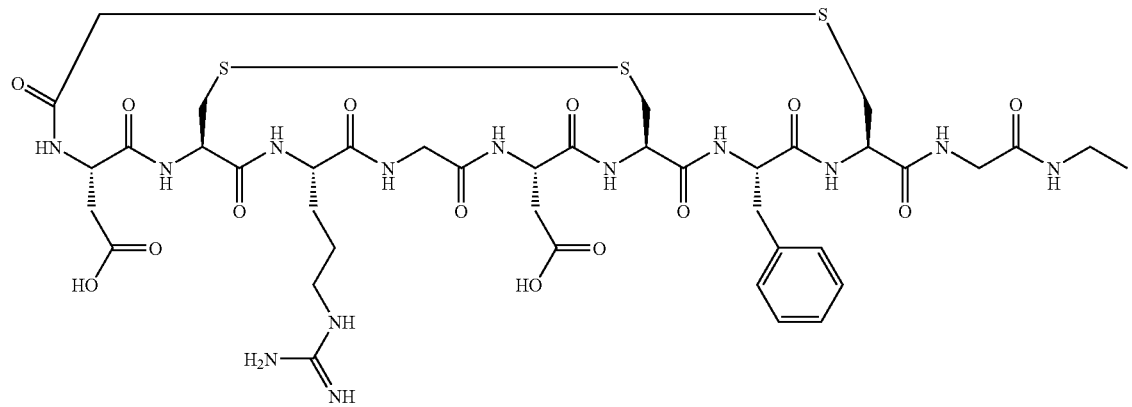

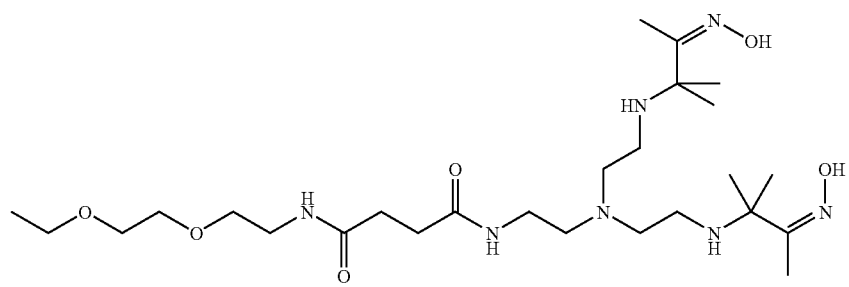

Molecular Weight = 1569.856
Exact Mass = 1568.690
Molecular Formula = C64H104N20O20S3

5 mg of Pn216 chelate active ester, 2 μl of N-methylmorpholine and 6 mg of [Cys$^{2-6}$]cyclo[CH$_2$CONH-Asp-Cys-Arg-Gly-Asp-Cys-Phe-Cys]-Gly-NH(CH$_2$CH$_2$O)$_2$CH$_2$CH$_2$NH$_2$ was dissolved in N,N-dimethylformamide (0.5 ml). The mixture was stirred for 24 hours.

Purification by preparative HPLC (Phenomenex Luna 5u C18 (2) 250×21.20 mm column) of the reaction mixture was carried out using 5-50% B, where A=H$_2$O/0.1% TFA and B=CH$_3$CN/0.1% TFA, over 40 min at a flow rate of 10 mL/min. After lyophilisation 3.5 mg of pure material was obtained (Analytical HPLC: Gradient, 5-50% B over 10 min where A=H$_2$O/0.1% TFA and B=CH$_3$CN/0.1% TFA; column, Phenomenex Luna 3μ C18 (2) 50×4.6 mm; detection, UV 214 nm; product retention time, 4.47 min). Further product characterisation was carried out using mass spectrometry: expected, M+H at 1569.7, found, at 1569.7).

2 g) The Compound May be Labelled with Technetium ($^{99m}$Tc) in a Manner Analogous to that Described in Example 1e) Above.

EXAMPLE 3

Fatty Acid Modified Vectors with Pn216 Chelate 3 a) Assembly of Dde-Lys-Cys(tBu)-Arg(Pmc)-Gly-Asp(OtBu)-Cys(tBu)-Phe-Cys(Trt)-Gly-(O-Bis-(aminoethyl) ethylene glycol trityl)resin (i)

The protected peptide was assembled on a ABI 433A automatic peptide synthesiser starting with O-Bis-(aminoethyl) ethylene glycol trityl resin on a 0.3 mmol scale using 1 mmol amino acid cartridges. The amino acids were pre-activated using HBTU before coupling.

3 b) Synthesis of ClCH$_2$CO-Lys(Hexanoyl)-Cys(tBu)-Arg-Gly-Asp-Cys(tBu)-Phe-Cys-Gly-NH—(CH$_2$CH$_2$O)$_2$CH$_2$CH$_2$NH$_2$ (ii)

0.1 mmol of resin (i) was treated with a solution of hexanoic anhydride in DMF for 17 hrs. The removal of Dde protecting groups from the resin was carried out using 2% hydrazine monohydrate in DMF for four times three minutes. The resin was then treated with a solution of chloroacetic anhydride in DMF for 60 min.

The simultaneous removal of peptide and side-chain protecting groups (except tBu) from the resin was carried out in TFA containing TIS (5%), H$_2$0 (5%) and phenol (2.5%) for two hours.

After work-up 100 mg of crude peptide was obtained (Analytical HPLC: Gradient, 5-50% B over 10 min where A=H$_2$O/0.1% TFA and B=CH$_3$CN/0.1% TFA; column, Phenomenex Luna 3μ C18 (2) 50×4.6 mm; flow, 2 ml/min; detection, UV 214 nm; product retention time, 7.81 min). Further product characterisation was carried out using mass spectrometry: expected, M+H at 1404.7, found, at 1404.6).

3 c) Synthesis of cyclo[CH$_2$CO-Lys(Hexanoyl)-Cys(tBu)-Arg-Gly-Asp-Cys(tBu)-Phe-Cys]-Gly-NH—(CH$_2$CH$_2$O)$_2$CH$_2$CH$_2$NH$_2$ (iii)

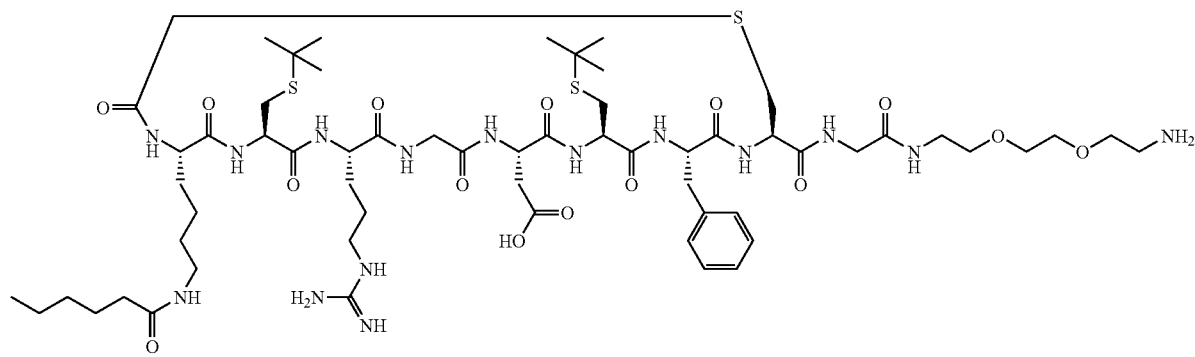

Molecular Weight = 1368.757
Exact Mass = 1367.676
Molecular Formula = C60H101N15O15S3

100 mg of compound (ii) was dissolved in water/acetonitrile. The mixture was adjusted to pH 8 with ammonia solution and stirred for 20 hours.

After work-up 104 mg of crude peptide was obtained (Analytical HPLC: Gradient, 5-50% B over 10 min where A=H$_2$O/0.1% TFA and B=CH$_3$CN/0.1% TFA; column, Phenomenex Luna 3μ C18 (2) 50×4.6 mm; flow, 2 ml/min; detection, UV 214 nm; product retention time, 7.67 min). Further product characterisation was carried out using mass spectrometry: expected, M+H at 1368.7, found, at 1368.7).

3 d) Synthesis of [Cys$^{2-6}$]cyclo[CH$_2$CO-Lys(Hexanoyl)-Cys-Arg-Gly-Asp-Cys-Phe-Cys]-Gly-NH—(CH$_2$CH$_2$O)$_2$CH$_2$CH$_2$NH$_2$ (iv)

Purification by preparative HPLC (Phenomenex Luna 5u C18 (2) 250×21.20 mm column) of the crude material was carried out using 5-50% B, where A=H$_2$O/0.1% TFA and B=CH$_3$CN/0.1% TFA, over 40 min at a flow rate of 10 mL/min. After lyophilisation 9 mg of pure material was obtained (Analytical HPLC: Gradient, 5-50% B over 10 min where A=H$_2$O/0.1% TFA and B=CH$_3$CN/0.1% TFA; column, Phenomenex Luna 3μ C18 (2) 50×4.6 mm; flow, 2 ml/min; detection, UV 214 nm; product retention time, 5.38 min). Further product characterisation was carried out using mass spectrometry: expected, M+H at 1254.5, found, at 1254.6).

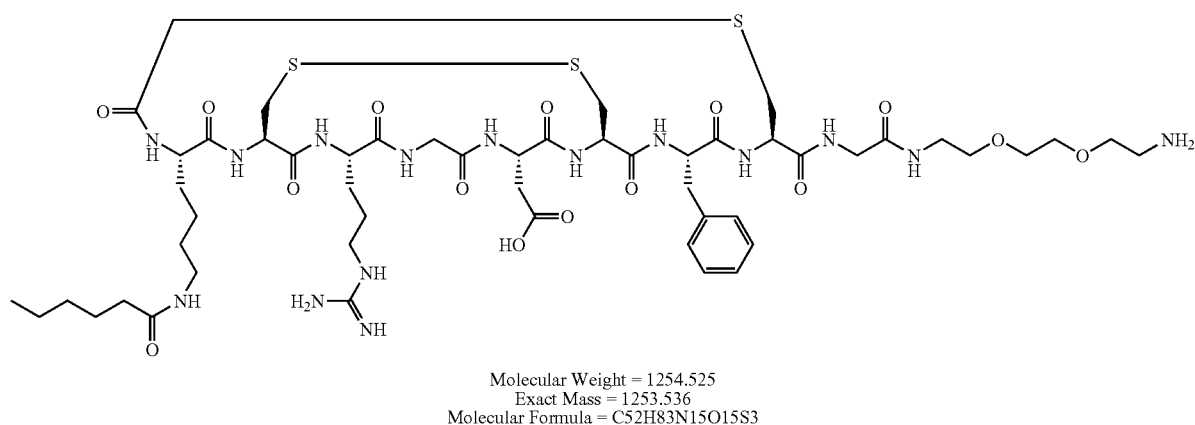 [SMILES: CCCCCC(=O)NCCCC[C@@H]1NC(=O)CSC[C@@H](C(=O)NCC(=O)NCCOCCOCCN)NC(=O)[C@H](Cc2ccccc2)NC(=O)[C@@H]2CSSC[C@H](NC1=O)C(=O)N[C@@H](CCCNC(=N)N)C(=O)NCC(=O)N[C@@H](CC(=O)O)C(=O)N2]

Molecular Weight = 1254.525
Exact Mass = 1253.536
Molecular Formula = C52H83N15O15S3

50 mg of compound (iii) was treated with a solution of anisole (100 μl), DMSO (1 ml) and TFA (50 ml) at room temperature for 30 min following which the TFA was removed in vacuo and the peptide precipitated by the addition of diethyl ether.

3 e) Synthesis of [Cys$^{2-6}$]cyclo[CH$_2$CO-Lys(Hexanoyl)-Cys-Arg-Gly-Asp-Cys-Phe-Cys]-Gly-NH—(CH$_2$CH$_2$O)$_2$CH$_2$CH$_2$NH-Pn216 (v)

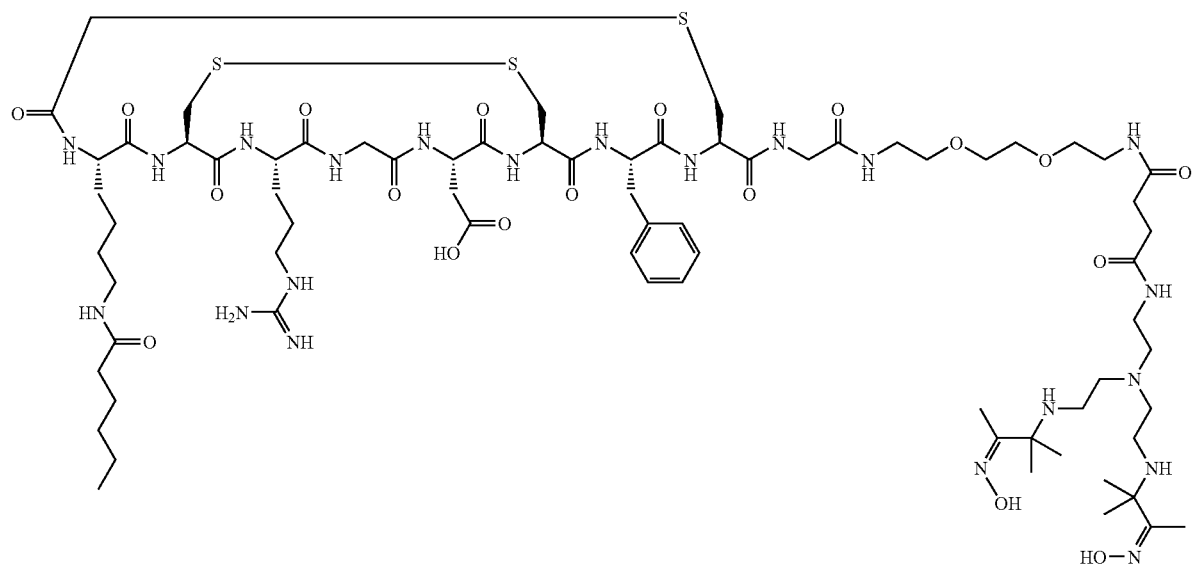

Molecular Weight = 1681.088
Exact Mass = 1679.831
Molecular Formula = C72H121N21O19S3

9 mg of compound (iv), 11 mg of Pn216 chelate active ester and 8 µl of N-methylmorpholine was dissolved in DMF (1 ml). The mixture was stirred for 3.5 hours.

Purification by preparative HPLC (Phenomenex Luna 5u C18 (2) 250×21.20 mm column) of the reaction mixture was carried out using 5-50% B, where A=H$_2$O/0.1% TFA and B=CH$_3$CN/0.1% TFA, over 40 min at a flow rate of 10 mL/min. After lyophilisation 5.2 mg of pure material was obtained (Analytical HPLC: Gradient, 5-50% B over 10 min where A=H$_2$O/0.1% TFA and B=CH$_3$CN/0.1% TFA; column, Phenomenex Luna 3µ C18 (2) 50×4.6 mm; flow, 2 ml/min; detection, UV 214 nm; product retention time, 5.83 min). Further product characterisation was carried out using mass spectrometry: expected, M+H at 1680.8, found, at 1680.7).

EXAMPLE 4

PEG Modified Vectors with Pn216 Chelate 4 a) Synthesis of ClCH$_2$CO-Lys(PEG2000)-Cys(tBu)-Arg-Gly-Asp-Cys(tBu)-Phe-Cys-Gly-NH—(CH$_2$CH$_2$O)$_2$CH$_2$CH$_2$NH$_2$ (vi)

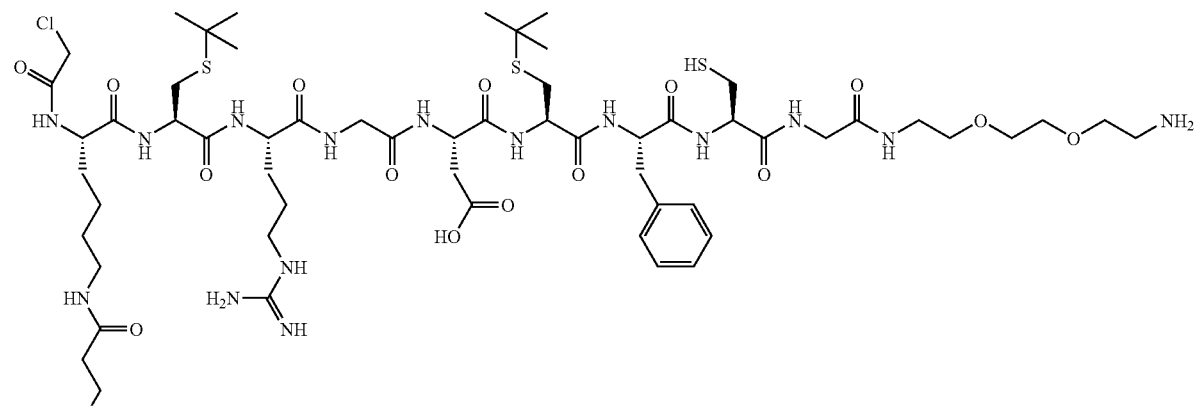

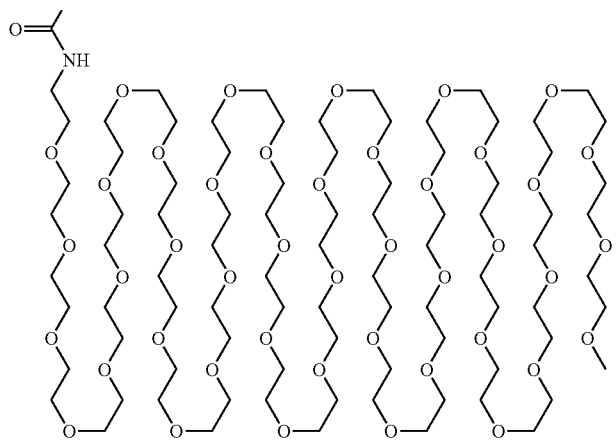

0.1 mmol of resin (i) was treated with CH₃O-PEG-NHCOCH₂CH₂COOH (pre-activated with HATU) for 16 hrs. The removal of Dde protecting groups from the resin was carried out using 2% hydrazine monohydrate in DMF for four times three minutes. The resin was then treated with a solution of chloroacetic anhydride in DMF for 60 min.

The simultaneous removal of peptide and side-chain protecting groups (except tBu) from the resin was carried out in TFA containing TIS (5%), H₂O (5%) and phenol (2.5%) for two hours.

After work-up 110 mg of crude peptide was obtained (Analytical HPLC: Gradient, 5-50% B over 10 min where A=H₂O/0.1% TFA and B=CH₃CN/0.1% TFA; column, Phenomenex Luna 3μ C18 (2) 50×4.6 mm; flow, 2 ml/min; detection, UV 214 nm; product retention time, multiple peaks from 5 to 9 min). Further product characterisation was carried out using MALDI mass spectrometry: expected, M+H at 3313, found, at 2785).

4 b) Synthesis of cyclo[CH₂CO-Lys (PEG2000)-Cys(tBu)-Arg-Gly-Asp-Cys(tBu)-Phe-Cys]-Gly-NH—(CH₂CH₂O)₂CH₂CH₂NH₂ (vii)

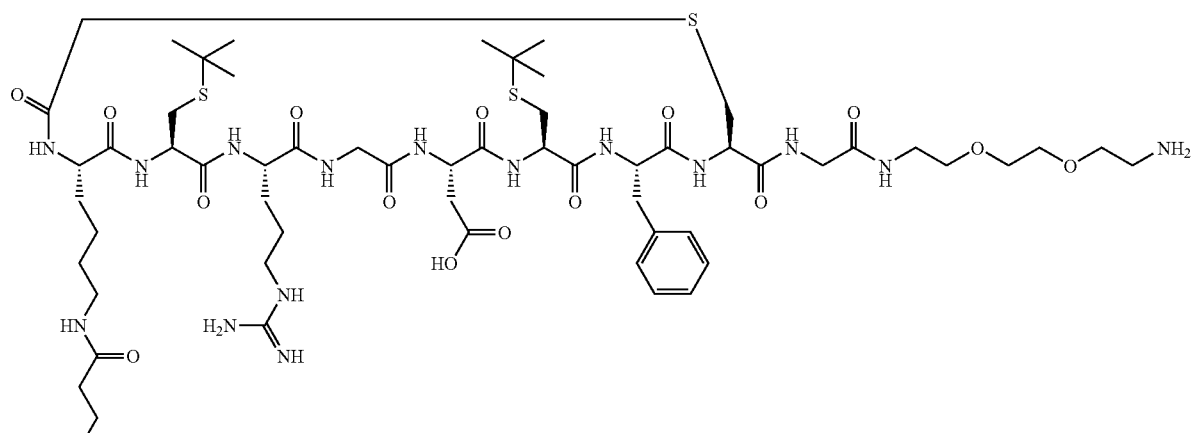

-continued

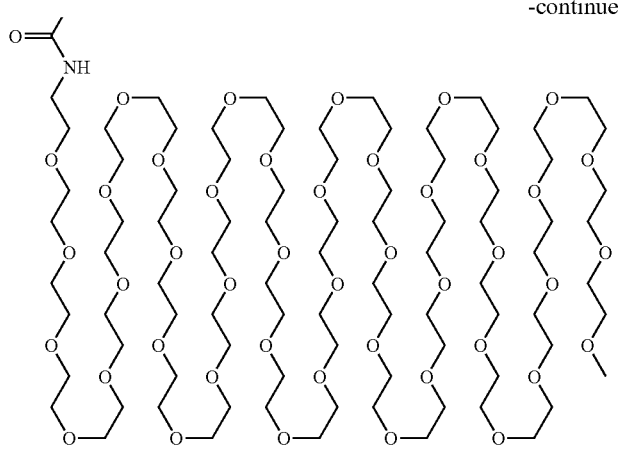

Molecular Weight = 3278.032
Exact Mass = 3275.778
Molecular Formula = C145H270N16O59S3

110 mg of compound (vi) was dissolved in water/acetonitrile. The mixture was adjusted to pH 8 with ammonia solution and stirred for 20 hours.

After work-up 90 mg of crude peptide was obtained (Analytical HPLC: Gradient, 5-50% B over 10 min where A=$H_2O$/0.1% TFA and B=$CH_3CN$/0.1% TFA; column, Phenomenex Luna 3μ C18 (2) 50×4.6 mm; flow, 2 ml/min; detection, UV 214 nm; product retention time, multiple peaks from 5 to 9 min). Further product characterisation was carried out using MALDI mass spectrometry: expected, M+H at 3277, found, at 2627).

4 c) Synthesis of [$Cys^{2-6}$]cyclo[$CH_2CO$-Lys(PEG2000)-Cys-Arg-Gly-Asp-Cys-Phe-Cys]-Gly-NH—($CH_2CH_2O)_2$ $CH_2CH_2NH_2$ (viii)

60 mg of compound (vii) was treated with a solution of anisole (200 μl), DMSO (2 ml) and TFA (100 ml) at room temperature for 30 min following which the TFA was removed in vacuo and the peptide precipitated by the addition of diethyl ether.

Purification by preparative HPLC (Phenomenex Luna 5u C18 (2) 250×21.20 mm column) of the crude material was carried out using 5-50% B, where A=$H_2O$/0.1% TFA and B=$CH_3CN$/0.1% TFA, over 40 min at a flow rate of 10 mL/min. After lyophilisation 30 mg of pure material was obtained (Analytical HPLC: Gradient, 5-50% B over 10 min where A=$H_2O$/0.1% TFA and B=$CH_3CN$/0.1% TFA; column, Phenomenex Luna 3μ C18 (2) 50×4.6 mm; flow, 2 ml/min; detection, UV 214 nm; product retention time, broad peak at 5 min).

4 d) Conjugation of [$Cys^{2-6}$]cyclo[$CH_2CO$-Lys(PEG2000)-Cys-Arg-Gly-Asp-Cys-Phe-Cys]-Gly-NH—($CH_2CH_2O)_2$ $CH_2CH_2NH_2$ with Pn216 Chelate (ix)

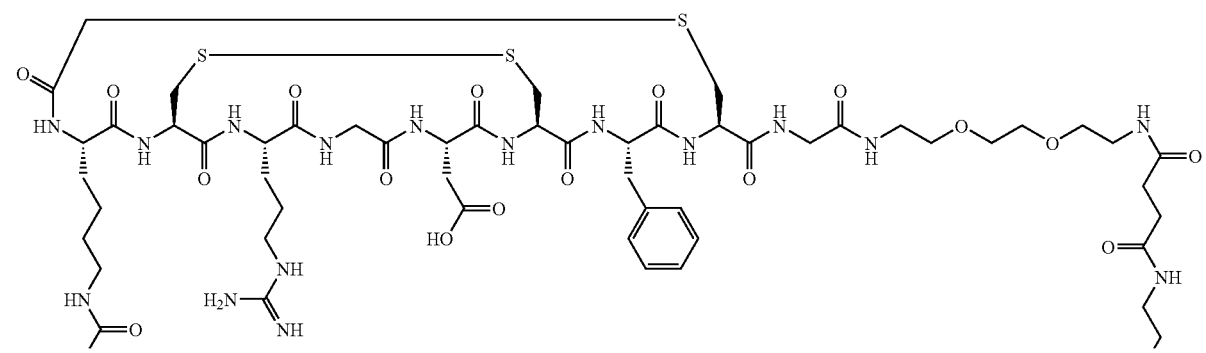

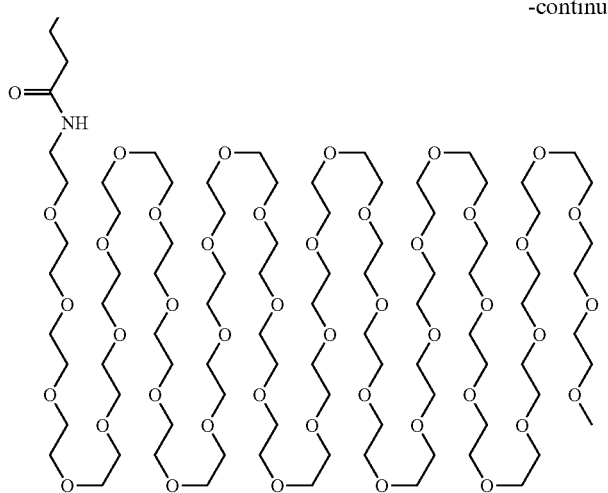
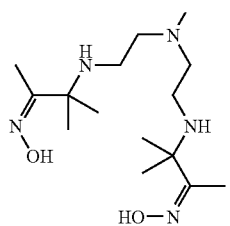

Molecular Weight = 3590.363
Exact Mass = 3587.933
Molecular Formula = C157H290N22O63S3

20 mg of compound (viii), 11 mg of Pn216 chelate active ester and 8 μl of NMM was dissolved in DMF (1 ml). The mixture was stirred for 24 hours.

Purification by preparative HPLC (Phenomenex Luna 5u C18 (2) 250×21.20 mm column) of the reaction mixture was carried out using 5-50% B, where A=$H_2O$/0.1% TFA and B=$CH_3CN$/0.1% TFA, over 40 min at a flow rate of 10 mL/min. After lyophilisation 10.7 mg of pure material was obtained (Analytical HPLC: Gradient, 5-50% B over 10 min where A=$H_2O$/0.1% TFA and B=$CH_3CN$/0.1% TFA; column, Phenomenex Luna 3μ C18 (2) 50×4.6 mm; flow, 2 ml/min; detection, UV 214 nm; product retention time, broad peak from 5 to 8 min). Further product characterisation was carried out using mass spectrometry: expected, M+H at 3589, found, at 3270).

EXAMPLE 5

Vectors with Pn44 Chelate 5 a) Preparation of 1,1,1-Tri(phenylsulphonyloxymethyl)ethane 1,1,1-Tris trihydroxymethyl (120 g, 1.0 mol) was dissolved in dichloromethane (1000 ml) and pyridine (237 g, 1 mol) and treated portionwise with phenylsulphonylchloride (528 g, 3 mol) at −5° C. on an ice/methanol bath at such a rate that the temperature did not rise above 10° C. The reaction was then allowed to warm to room temperature overnight. The reaction was then shaken with 5N hydrochloric acid and the organic phase separated, the aqueous phase was reextracted with dichloromethane and the organic extracts combined. The dichloromethane solution was dried over sodium sulphate and concentrated in vacuo to give 1,1,1-Tri(phenylsulphonyloxymethyl)ethane (540 g, 1 mol) as a gum.

5 b) Preparation of 1,1,1-tri(azidomethyl)ethane 1,1,1-Tri(phenylsulphonyloxymethyl)ethane (25 g, 70 mmol) in dimethylformamide (300 ml) was treated with sodium azide (41 g, 630 mmol, 9 eq) in a 500 ml RB flask and the mixture was heated at 120° with stirring for 7 hours. The reaction was then allowed to cool to room temperature and 50% saturated brine solution (250 ml) and diethylether (250 ml) added. The organic layer was separated washed with 50% saturated brine solution (250 ml) and dried over $Na_2SO_4$ and concentrated to give 1,1,1-tri(azidomethyl)ethane as a yellow viscous liquid (5.51 g, 28.2 mmol, 40% yield)

NMR $H^1$ ($CDCl_3$), 1.0 (3H, s, $CH_3$), 3.3 (6H, s, $CH_3$)

5 c) Preparation of 1,1,1-tri(aminomethyl)ethane 1,1,1-tri(azidomethyl)ethane (5.51 g, 28.2 mmol) in ethanol (140 ml) was treated with 10% palladium on charcoal (2 g) and hydrogenated at atmospheric pressure for 15 h under a flow of hydrogen to remove the liberated nitrogen. The reaction was filtered through a celite pad to remove the catalyst and concentrated in vacuum to give 1,1,1-tri(aminomethyl)ethane (2.53 g, 21.6 mmol, 76% yield) as a yellow liquid.

NMR $H^1$ ($CDCl_3$), 0.8 (3H, s, $CH_3$), 1.18 (6H, s, 3×$NH_2$), 2.6 (6H, s, 3×$CH_2$).

NMR $C^{13}$ ($CDCl_3$), 20.1 $CH_3$, 31.7 C, 48.8 $CH_2$.

5 d) Preparation of Pn44

To a suspension of 3-chloro-3-methyl-2-nitrosobutane (23.14 g, 1706 mmol, 2 eq) in dry methanol (50 ml) under nitrogen at 0° C. was added slowly a solution of 1,1,1-tri(aminomethyl)ethane (10 g, 85.3 mmol) in dry methanol (10 ml). The mixture was stirred at 0° C. for 40 mins, warmed to room temperature, and then heated to 60° C. for 3 hrs. The reaction mixture was then allowed to cool to room temperature and was stirred for 5 days. The mixture was finally heated to reflux temperature for 3 hours, after which the solvent was removed in vacuo. The residue was dissolved in 2M HCl (150 ml) and extracted with ether (3×100 ml). Then aqueous layer was then basified to pH10 using 6M NaOH and was extracted with dichloromethane (3×100 ml). The combined organic layers were left to stand at room temperature and a white solid precipitated out. This solid was filtered off, and was shown to be the tri-adduct by NMR. The filtrate was concentrated to ~⅓ and was left to stand in a refrigerator. Another white solid precipitated from the solution. This was isolated by filtration and was shown to be Pn44 by $^1$H-NMR. The filtrate was again concentrated and a further portion of Pn44 crystallised out from the solution. (Total yield 6.981 g, 26%).

NMR (H$^1$ CDCl$_3$), 0.9 (3H, s, CH$_3$), 1.25 (6H, d, 4×CH$_3$), 1.8 (6H, s, 2×CH$_3$), 2.4 (2H, d, 2×CH), 2.54 (2H, d, 2×CH), 2.95 (2H, s, CH$_2$), 4.95, (6H, s, OH).

MS C$_{15}$H$_{33}$N$_5$O$_2$ M+H=316 Found 316

5 e) Synthesis of PN44-Succinic Acid Intermediate

As for example 2c.

5 f) Synthesis of Tetrafluorothiophenol Ester Derivative of PN44-Succinic Acid

As for example 2d.

5 g) Synthesis of [Cys$^{2-6}$]cyclo[CH$_2$CONH-Asp-Cys-Arg-Gly-Asp-Cys-Phe-Cys]-Gly-NH(CH$_2$CH$_2$O)$_2$CH$_2$CH$_2$NH$_2$ See example 1a-1c.

5 h) Synthesis of [Cys-]cyclo[CH$_2$CONH-Asp-Cys-Arg-Gly-Asp-Cys-Phe-Cys]-Gly-NH(CH$_2$CH$_2$O)$_2$CH$_2$CH$_2$NH-Pn44

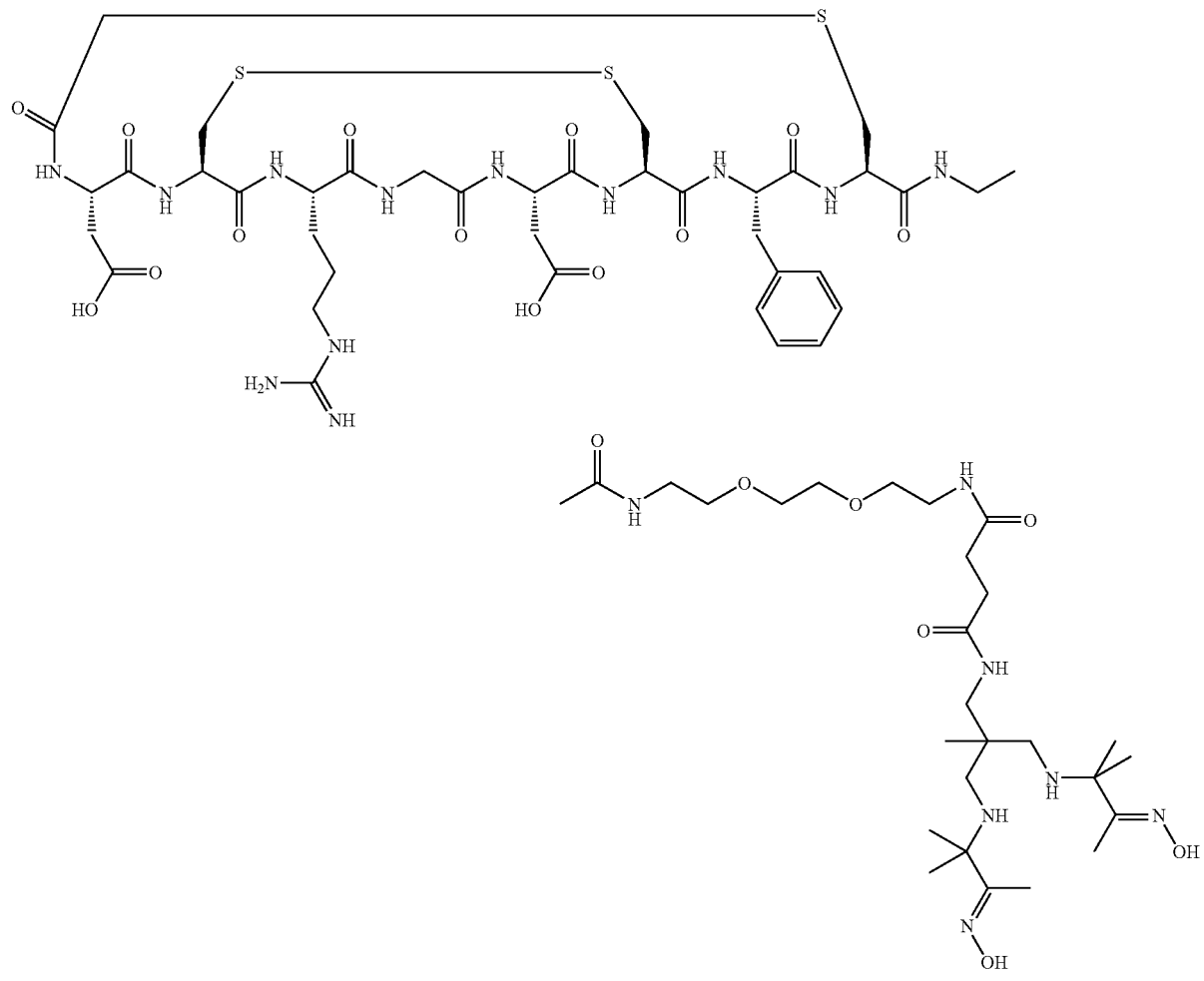

Molecular Weight = 1540.815
Exact Mass = 1539.663
Molecular Formula = C63H101N19O20S3

7 mg of Pn44 chelate active ester, 5 μl of NMM and 10 mg of [Cys$^{2-6}$]cyclo[CH$_2$CONH-Asp-Cys-Arg-Gly-Asp-Cys-Phe-Cys]-Gly-NH(CH$_2$CH$_2$O)$_2$CH$_2$CH$_2$NH$_2$ was dissolved in NMP (1 ml). The mixture was stirred for 3 hours.

Purification by preparative HPLC (Phenomenex Luna 5μ C18 (2) 250×21.20 mm column) of the reaction mixture was carried out using 5-50% B, where A=H$_2$O/0.1% TFA and B=CH$_3$CN/0.1% TFA, over 40 min at a flow rate of 10 mL/min. After lyophilisation 9.8 mg of pure material was obtained (Analytical HPLC: Gradient, 5-50% B over 10 min where A=H$_2$O/0.1% TFA and B=CH$_3$CN/0.1% TFA; column, Phenomenex Luna 3μ C18 (2) 50×4.6 mm; flow, 2 ml/min; detection, UV 214 nm; product retention time, 4.38 min). Further product characterisation was carried out using mass spectrometry: expected, M+H at 1540.7, found, at 1540.6).

EXAMPLE 6
Synthesis of bis-[$Cys^{2-6}$], cyclo[-$CH_2CONH$-Asp-$Cys^2$-Arg-Gly-Asp-$Cys^6$-Phe-Cys]-Ahx-Lys(cyclo[-$CH_2CONH$-Asp-$Cys^2$-Arg-Gly-Asp-$Cys^6$-Phe-Cys]Ahx)-$NH(CH_2CH_2O)_2CH_2CH_2NH$-Pn216
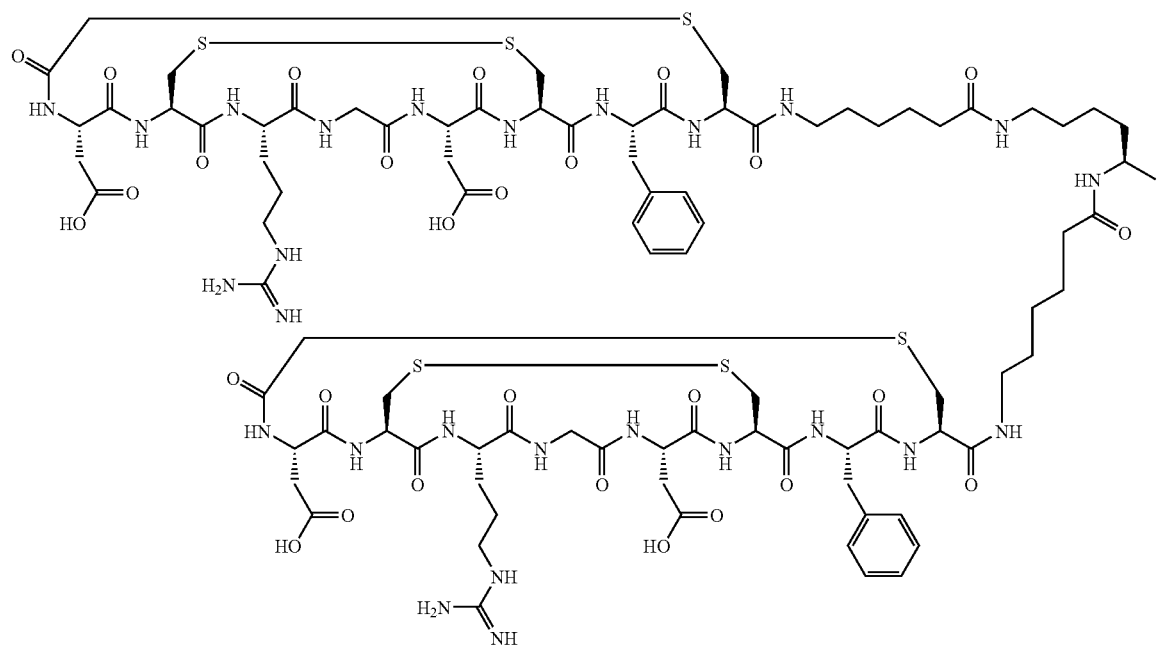
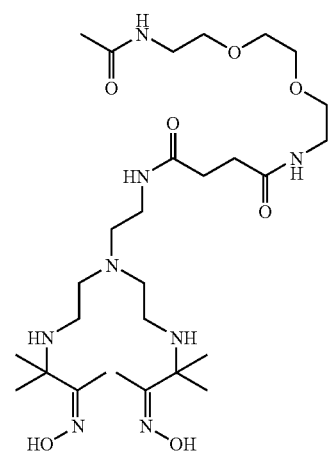

The dimer peptide was assembled on a ABI 433A automatic peptide synthesiser starting with O-Bis(aminoethyl) ethylene glycol trityl resin on a 0.1 mmol scale using 1 mmol amino acid cartridges. The amino acids were pre-activated using HBTU before coupling in the order Fmoc-Lys(Fmoc)-OH, Fmoc-Ahx-OH (Ahx=aminohexanoic acid), Fmoc-Cys(Trt)-OH, Fmoc-Phe-OH, Fmoc-Cys(tBu)-OH, Fmoc-Asp(O-tBu)-OH, Fmoc-Gly-OH, Fmoc-Arg(Pmc)-OH, Fmoc-Cys(tBu)-OH, Fmoc-Asp(O-tBu)-OH, chloroacetic acid anhydride. The semi-protected peptide was then cleaved from the solid support in TFA containing 5% TIS, 5% phenol and 5% water. The crude chloro-peptide was then cyclised in 20% acetonitrile/water (pH 8) yielding the monocyclic t-Butyl protected intermediate (shown below) after HPLC purification on a Vydac C18 column.

To the pure intermediate was added a solution of 10% DMSO/TFA containing 0.1 mL of anisole. The peptide mixture was stirred for 1 h and excess TFA evaporated before precipitation of the product (shown below) by addition of diethyl ether.

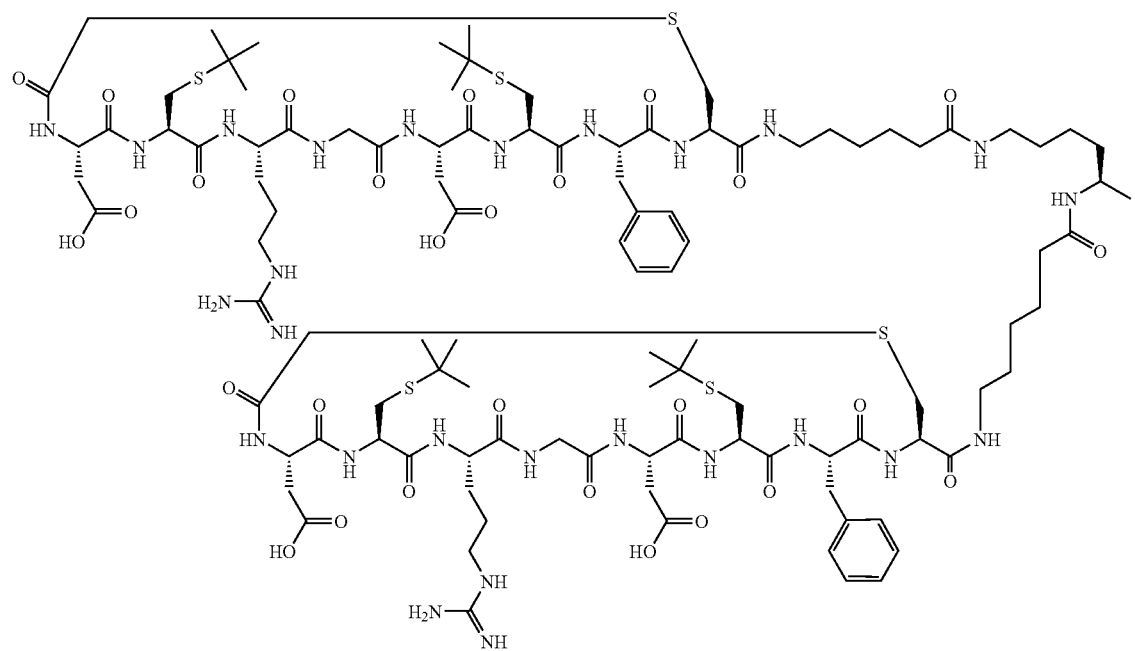

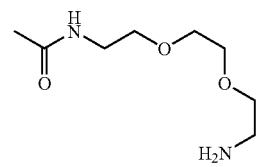

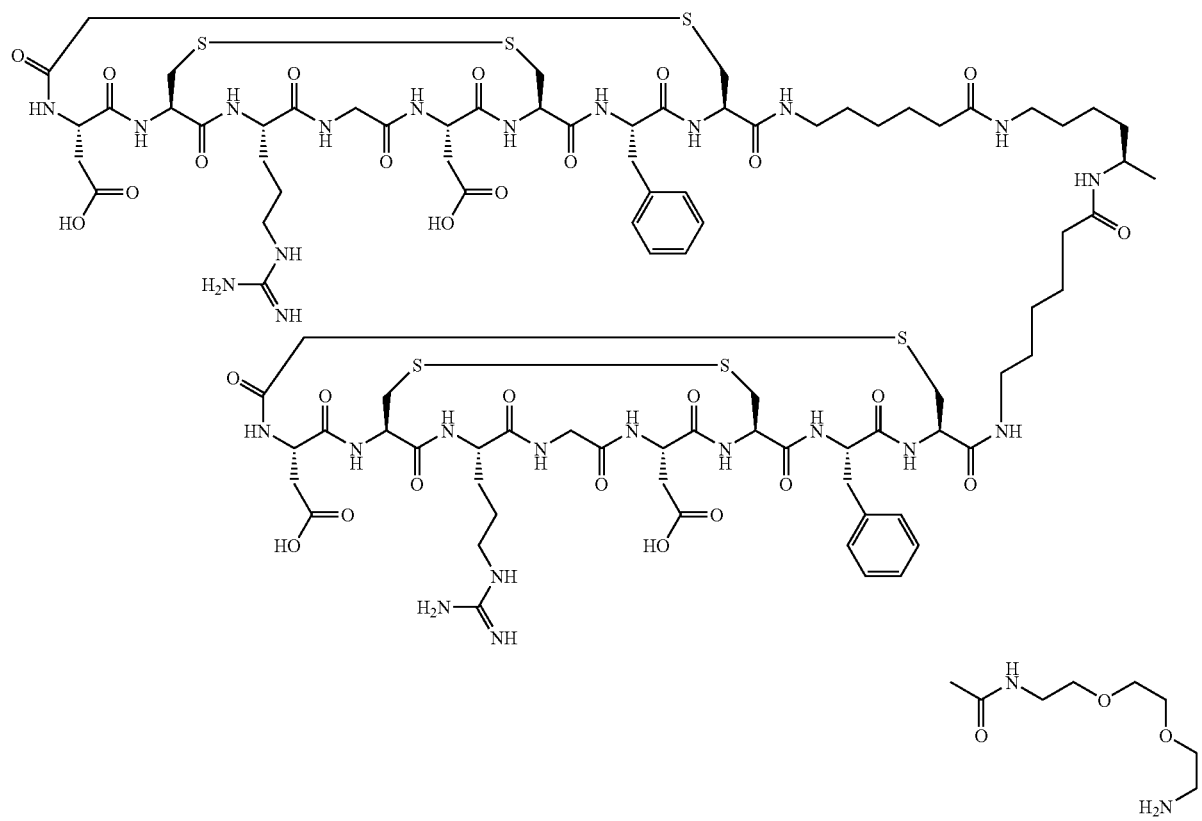

This product (5 mg) was then dissolved in 1 mL of DMF containing 2% NMM and 5 mg of the Pn216 active ester from example 1 added. The conjugation reaction was followed by HPLC and found to be complete after 16 hours. The peptide solution was then diluted with water to a total of 8 mL and charged on a Phenomenex Luna 5μ C18 (2) 250×10 mm column using a 5-50% B gradient, where A=$H_2O$/0.1% TFA and B=$CH_3CN$/0.1% TFA, over 30 min and a flow rate of 5 mL/min. After lyophilisation 2 mg of desired end product was obtained (Analytical HPLC: Gradient, 5-50% B over 10 min where A=$H_2O$/0.1% TFA and B=$CH_3CN$/0.1% TFA; column, Phenomenex Luna 3μ C18 (2) 50×4.6 mm; flow, 2 ml/min; detection, UV 214 nm; product retention time, 9.8 min). Further product characterisation was carried out using ES-MS: expected, M+H at 1805, found, at 1805.

What is claimed is:

1. A compound of formula I

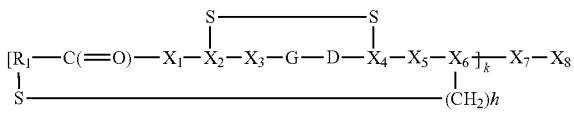

or a pharmaceutically acceptable salt thereof,
wherein
G represents glycine;
D represents aspartic acid;
$R_1$ represents $-(CH_2)_n-$ or $-(CH_2)_n-C_6H_4-$ wherein n represents a positive integer 1 to 10, and h represents a positive integer 1 or 2;
$X_1$ represents a bond or 1 to 5 amino acid residues wherein each amino acid residue independently optionally can be derivatized with a functional side-chain chosen from $C_{1-22}$ alkyl, $C_{1-22}$ perfluoroalkyl or polyethyleneglycol;
$X_2$ and $X_4$ represent independently an amino acid residue capable of forming a disulfide bond;
$X_3$ represents arginine, N-methylarginine or an arginine mimetic;
$X_5$ represents a hydrophobic amino acid;
$X_6$ represents a thiol-containing amino acid residue;
k represents a positive integer 1 to 10;
$X_7$ represents an amino acid residue; and
$X_8$ is absent.

2. A pharmaceutical composition comprising an effective amount of the compound of general formula (I), according to claim 1, or a pharmaceutically acceptable salt thereof, together with one or more pharmaceutically acceptable adjuvants, excipients or diluents.

3. A compound as claimed in claim 1 for the manufacture of a contrast medium for use in a method of diagnosis involving administration of said contrast medium to an animate subject and generation of an image of at least part of said subject.

* * * * *